United States Patent
Masuda et al.

(10) Patent No.: US 10,281,458 B2
(45) Date of Patent: May 7, 2019

(54) BLOOD ANALYZER, BLOOD ANALYZING METHOD, AND NON-TRANSITORY COMPUTER-READABLE STORAGE MEDIUM

(71) Applicant: SYSMEX CORPORATION, Kobe-shi, Hyogo (JP)

(72) Inventors: Yuji Masuda, Kobe (JP); Konobu Kimura, Kobe (JP)

(73) Assignee: SYSMEX CORPORATION, Kobe-shi (JP)

(*) Notice: Subject to any disclaimer, the term of this patent is extended or adjusted under 35 U.S.C. 154(b) by 1 day.

(21) Appl. No.: 15/262,738

(22) Filed: Sep. 12, 2016

(65) Prior Publication Data
US 2017/0074863 A1    Mar. 16, 2017

(30) Foreign Application Priority Data
Sep. 14, 2015 (JP) .............................. 2015-181055

(51) Int. Cl.
*G01N 1/30* (2006.01)
*G01N 1/38* (2006.01)
(Continued)

(52) U.S. Cl.
CPC .......... *G01N 33/5094* (2013.01); *G01N 1/30* (2013.01); *G01N 1/38* (2013.01); *G01N 15/1429* (2013.01);
(Continued)

(58) Field of Classification Search
CPC .......... G01N 15/1429; G01N 15/1436; G01N 15/1459; G01N 1/30; G01N 1/38;
(Continued)

(56) References Cited

U.S. PATENT DOCUMENTS

2009/0111118 A1    4/2009    Mylvaganam et al.
2010/0248300 A1*   9/2010    Yoshida ............. G01N 15/1459
                                                                435/39
(Continued)

FOREIGN PATENT DOCUMENTS

CA    2708692 A1    12/2011
JP    2002-148261 A    5/2002
(Continued)

OTHER PUBLICATIONS

Machine translation of Detailed Description of JP 2002-148261 published May 22, 2002, 12 pages.*
(Continued)

*Primary Examiner* — Gordon J Stock, Jr.
(74) *Attorney, Agent, or Firm* — Metrolexis Law Group, PLLC

(57) ABSTRACT

Disclosed is a blood analyzer including a specimen preparation unit that prepares a measurement specimen by mixing a hemolytic agent that hemolyzes red blood cells, a staining dye that dyes nucleic acids, and a blood specimen; a detector that detects intensity of side scattered light and intensity of fluorescence generated with application of light from the measurement specimen prepared by the specimen preparation unit; and an analysis unit that discriminates white blood cells from giant platelets based on the intensity of side scattered light and the intensity of fluorescence detected by the detector, and counts the white blood cells.

15 Claims, 14 Drawing Sheets

(51) Int. Cl.
  *G01N 15/00* (2006.01)
  *G01N 15/10* (2006.01)
  *G01N 15/14* (2006.01)
  *G01N 21/47* (2006.01)
  *G01N 21/64* (2006.01)
  *G01N 33/49* (2006.01)
  *G01N 33/50* (2006.01)

(52) U.S. Cl.
  CPC ..... *G01N 15/1436* (2013.01); *G01N 15/1459* (2013.01); *G01N 21/47* (2013.01); *G01N 21/6428* (2013.01); *G01N 33/4915* (2013.01); *G01N 2015/008* (2013.01); *G01N 2015/0084* (2013.01); *G01N 2015/1006* (2013.01); *G01N 2015/1402* (2013.01); *G01N 2015/1486* (2013.01); *G01N 2021/6439* (2013.01); *G01N 2201/0612* (2013.01); *G01N 2201/12* (2013.01)

(58) Field of Classification Search
  CPC ..... G01N 2015/008; G01N 2015/0084; G01N 2015/1006; G01N 2015/1402; G01N 2015/1486; G01N 2021/6439; G01N 21/47; G01N 21/6428; G01N 21/6486; G01N 2201/0612; G01N 2201/12; G01N 33/4915; G01N 33/5094; G01N 2021/6463; G01N 2021/6465; G01N 2021/6467; G01N 2021/4704; G01N 2021/4707; G01N 2021/4709; G01N 2021/4711; G01N 2021/4726; G01N 15/10; G01N 15/14; G01N 15/1431; G01N 15/1434; G01N 15/147; G01N 15/02; G01N 15/0205; G01N 15/0211; G01N 15/05; G01N 2015/1081; G01N 2015/1087; G01N 2015/1093; G01N 2015/1477; G01N 2015/1481; G01N 2015/1488; G01N 2015/149; G01N 2015/1493; G01N 2015/1495; G01N 2015/1497; G01N 2015/0069; G01N 2015/0065; G01N 2015/0238; G01N 2015/025; G01N 2015/0288; G01N 2015/0294; G01N 2015/03
  See application file for complete search history.

(56) References Cited

U.S. PATENT DOCUMENTS

| | | | |
|---|---|---|---|
| 2010/0330565 | A1 | 12/2010 | Narikawa et al. |
| 2011/0054807 | A1* | 3/2011 | Mizumoto ....... G01N 35/00623 702/35 |

FOREIGN PATENT DOCUMENTS

| | | |
|---|---|---|
| JP | 2007-071890 A | 3/2007 |
| JP | 2010-249796 A | 11/2010 |

OTHER PUBLICATIONS

Vizcaino, Gilberto J. et al., "Thrombocytopenic Purpura With Giant Platelets and Ultrastructural Platelet Defects," 1983, American Journal of Hematology 15: 89-95.*

* cited by examiner

FIG. 16

BLOOD ANALYZER, BLOOD ANALYZING METHOD, AND NON-TRANSITORY COMPUTER-READABLE STORAGE MEDIUM

CROSS REFERENCE TO RELATED APPLICATIONS

This application claims priority to prior Japanese Patent Application No. 2015-181055 filed on Sep. 14, 2015 entitled "BLOOD ANALYZER, BLOOD ANALYZING METHOD, AND COMPUTER PROGRAM" the entire contents of which are hereby incorporated by reference.

BACKGROUND

The disclosure relates to a blood analyzer, a blood analyzing method, and a computer program for discriminating between white blood cells and giant platelets using a measurement specimen prepared from blood.

Patent Literature 1 discloses a blood analyzer configured to discriminate white blood cells from abnormal blood cells contained in a blood specimen, and to detect the presence or absence of the abnormal blood cells. The blood analyzer prepares a measurement specimen for measuring the number of white blood cells in CBC (Complete Blood Count) item by mixing a blood specimen, a hemolytic agent, and a staining reagent. The blood analyzer introduces the measurement specimen into a flow cell, applies light onto the measurement specimen flowing through the flow cell, and detects forward scattered light and fluorescence generated from the measurement specimen. The blood analyzer uses intensity of the forward scattered light and intensity of the fluorescence to discriminate a particle group of white blood cells from a particle group of abnormal blood cells in platelets.

[Patent Literature 1] Japanese Patent Application Publication No. 2010-249796 (corresponding to United States Patent Application Publication No. 2010/0248300)

SUMMARY

A blood specimen of a subject with a disease such as Bernard-Soulier syndrome or May-Hegglin anomaly contains giant platelets having a structure called "pseudo-nucleus" with aggregated granules, and having substantially the same size as that of white blood cells. The blood analyzer disclosed in Patent Literature 1 may fail to accurately discriminate white blood cells from abnormal blood cells in a blood specimen containing those giant platelets. Therefore, it is desired to improve the accuracy of discrimination between white blood cells and giant platelets.

A blood analyzer according to a first aspect of embodiments includes a specimen preparation unit, a detector, and an analysis unit. The specimen preparation unit prepares a measurement specimen by mixing a hemolytic agent that hemolyzes red blood cells, a staining dye that dyes nucleic acids, and a blood specimen. The detector detects intensity of side scattered light and intensity of fluorescence generated with application of light from the measurement specimen prepared by the specimen preparation unit. The analysis unit discriminates white blood cells from giant platelets based on the intensity of side scattered light and the intensity of fluorescence detected by the detector, and counts the white blood cells.

A blood analyzing method according to a second aspect of embodiments includes applying light onto a measurement specimen in which red blood cells are hemolyzed and nucleic acids in blood cells are stained. The blood analyzing method includes: detecting intensity of side scattered light and intensity of fluorescence generated from the measurement specimen with the application of the light; and discriminating white blood cells from giant platelets based on the detected intensity of side scattered light and intensity of fluorescence, and counting the white blood cells.

A non-transitory computer-readable storage medium according to a third aspect of embodiments carrying one or more sequences of one or more instructions which, when executed by one or more processors, are configured to cause a computer connected to a measurement unit that measures a blood specimen to perform operations including acquiring measured data obtained by detecting intensity of side scattered light and intensity of fluorescence generated from a measurement specimen in which red blood cells are hemolyzed and nucleic acids in blood cells are stained; and discriminating white blood cells from giant platelets based on the intensity of side scattered light and the intensity of fluorescence in the acquired measured data, and counting the white blood cells.

A blood analyzer according to a fourth aspect of embodiments includes a specimen preparation unit, a detector, a display unit, and an analysis unit. The specimen preparation unit prepares a measurement specimen by mixing a hemolytic agent that hemolyzes red blood cells, a staining dye that dyes nucleic acids, and a blood specimen. The detector detects intensity of side scattered light and intensity of fluorescence generated when light is applied onto the measurement specimen prepared by the specimen preparation unit. The analysis unit detects giant platelets in the measurement specimen based on the intensity of side scattered light and the intensity of fluorescence detected by the detector, and displays information suggesting presence of the giant platelets on the display unit.

A blood analyzing method according to a fifth aspect of embodiments includes: applying light onto a measurement specimen in which red blood cells are hemolyzed and nucleic acids in blood cells are stained; detecting intensity of side scattered light and intensity of fluorescence generated from the measurement specimen with the application of the light; and detecting giant platelets in the measurement specimen based on the detected intensity of side scattered light and intensity of fluorescence, and outputting information suggesting presence of the giant platelets.

A blood analyzer according to a sixth aspect of embodiments a specimen preparation unit, a detector, an analysis unit, and a display unit. The specimen preparation unit prepares a measurement specimen by mixing a hemolytic agent that hemolyzes red blood cells, a staining dye that dyes nucleic acids, and a blood specimen. The detector detects intensity of forward scattered light, intensity of side scattered light, and intensity of fluorescence generated with application of light from the measurement specimen prepared by the specimen preparation unit. The analysis unit can execute first discrimination processing of discriminating white blood cells from other particles in the measurement specimen, based on the intensity of forward scattered light and the intensity of fluorescence detected by the detector, and of counting the white blood cells, and second discrimination processing of discriminating white blood cells from other particles in the measurement specimen, based on the intensity of side scattered light and the intensity of fluorescence detected by the detector, and of counting the white blood cells. Moreover, the analysis unit causes the display unit to display the number of white blood cells obtained by the first discrimination processing when the result of the first discrimination processing does not meet a predetermined condition, and the analysis unit causes the display unit to display the number of white blood cells obtained by the second discrimination processing when the result of the first discrimination processing meets the predetermined condition.

BRIEF DESCRIPTION OF DRAWINGS

FIG. 16 is a diagram illustrating a display example of an analysis result.

EMBODIMENTS

In this embodiment, description is given of a blood analyzer configured to discriminate between white blood cells and giant platelets in a measurement specimen prepared from a reagent, based on intensity of side scattered light and intensity of fluorescence generated from a blood specimen and the measurement specimen with application of light.

Configuration of Blood Analyzer

Figure 1:
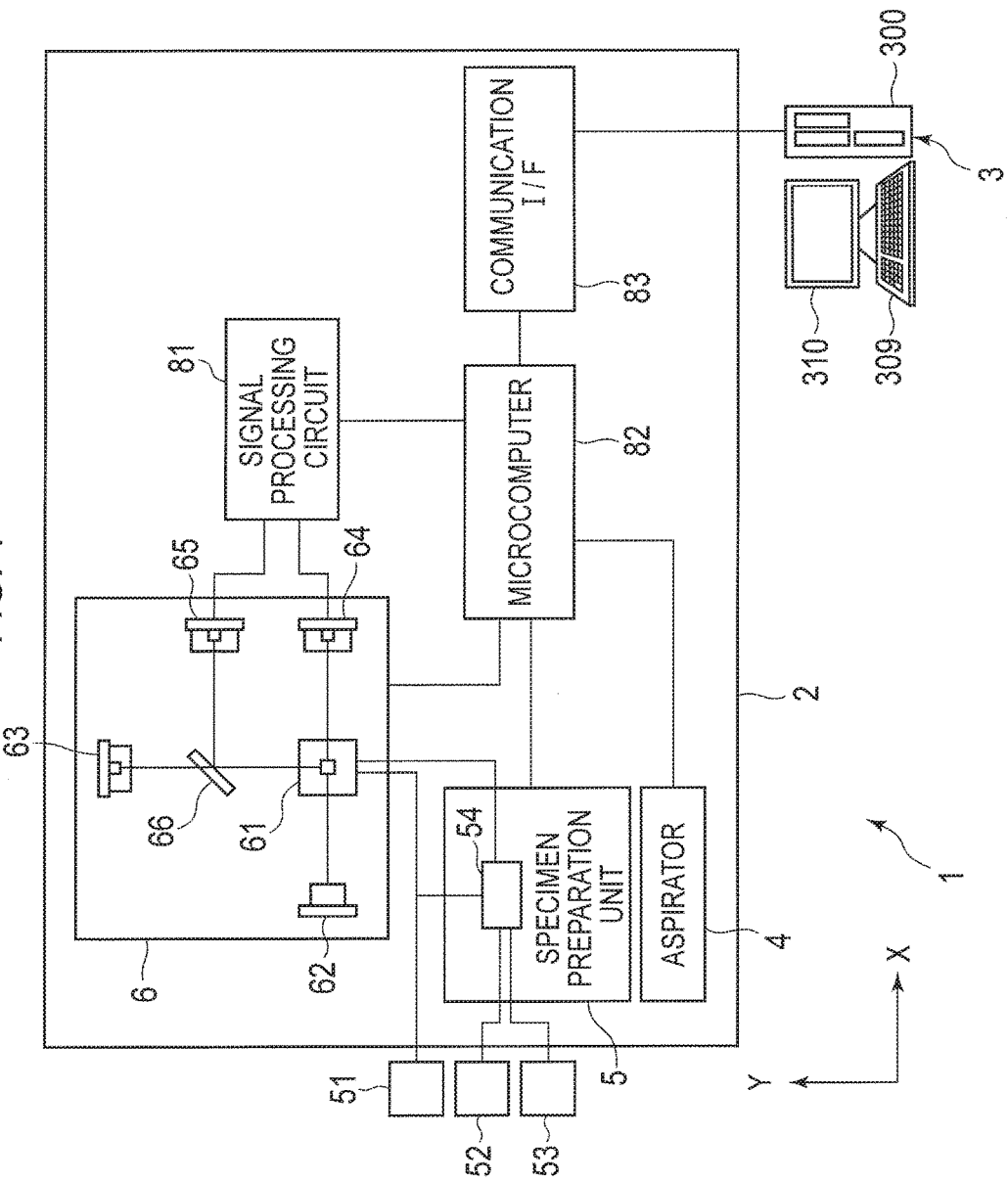
FIG. 1 is a schematic diagram illustrating a configuration of a blood analyzer according to an embodiment.

With reference to FIG. 1, a configuration of a blood analyzer is described. Blood analyzer 1 includes measurement unit 2 and analysis unit 3. Measurement unit 2 takes in a blood specimen, prepares a measurement specimen from the blood specimen, and optically measures the measurement specimen. Analysis unit 3 processes measured data obtained from the measurement by measurement unit 2, and displays the analysis result of the blood specimen.

Measurement unit 2 includes aspirator 4, specimen preparation unit 5, detector 6, signal processing circuit 81, microcomputer 82, and communication interface 83.

Aspirator 4 has an unillustrated aspiration tube, and aspirates the blood specimen housed in a test tube through the aspiration tube.

Specimen preparation unit 5 has reaction tank 54 and is connected to reagent containers 51, 52, and 53. Reagent container 51 houses a diluent. Reagent container 52 houses a hemolytic agent that hemolyzes red blood cells. Reagent container 53 houses a staining reagent containing a staining dye that dyes nucleic acids. Aspirator 4 moves the aspiration tube to above reaction tank 54, and discharges the aspirated blood specimen into reaction tank 54. Specimen preparation unit 5 mixes the blood specimen, the hemolytic agent, and the staining reagent in reaction tank 54 to prepare a measurement specimen. The measurement specimen is used for measurement of white blood cells.

The diluent housed in reagent container 51 is used as a sheath liquid in blood cell measurement by flow cytometry.

The hemolytic agent housed in reagent container 52 is described. The hemolytic agent contains a surfactant, which hemolyzes red blood cells and damages cell membranes of white blood cells. The hemolytic agent has a pH of preferably 2.0 to 4.5, more preferably 2.0 to 3.5. To be more specific, the hemolytic agent contains a cationic surfactant and a nonionic surfactant. The concentration of the cationic surfactant is preferably 300 mg/L to 9000 mg/L, more preferably 400 mg/L to 8000 mg/L, most preferably 500 mg/L to 7000 mg/L, but can be appropriately adjusted according to the type of the cationic surfactant to be used. The concentration of the nonionic surfactant is preferably 500 mg/L to 7000 mg/L, more preferably 800 mg/L to 6000 mg/L, most preferably 1000 mg/L to 5000 mg/L, but can be appropriately adjusted according to the type of the nonionic surfactant to be used. Moreover, the hemolytic agent may contain aromatic carboxylic acid or a salt thereof. The concentration of the aromatic carboxylic acid or a salt thereof in the hemolytic agent is not particularly limited as long as the pH of the hemolytic agent is within the above range, and is preferably 0.1 mM to 100 mM, more preferably 0.5 mM to 50 mM. Note that, as for a specific composition of the hemolytic agent, one described in U.S. Patent Application Publication No. 2010/330565 can be used. Moreover, as the hemolytic agent, Lysercell WNR manufactured by Sysmex Corporation can be used.

The staining reagent contained in reagent container 53 is described. The staining reagent contains a staining dye. By mixing the hemolytic agent, the staining reagent, and the blood specimen, the staining dye enters cells having damaged cell membranes, thereby staining nucleic acid and organelle. A fluorescent dye is not particularly limited as long as the dye can stain the nucleic acid and is one generally used in the field of the disclosure. As for a specific composition of the staining reagent, one described in U.S. Patent Application Publication No. 2010/330565 can be used. Moreover, as the staining reagent, Fluorocell WNR manufactured by Sysmex Corporation can be used.

Note that the measurement specimen may be prepared by mixing the blood specimen with one reagent containing a staining dye and a hemolytic agent that hemolyzes red blood cells, rather than separating the hemolytic agent and the staining reagent.

Detector 6 is used for measurement of white blood cells by flow cytometry. Detector 6 includes flow cell 61, light source unit 62, and light receivers 63, 64, and 65. The diluent housed in reagent container 51 and the measurement specimen prepared by specimen preparation unit 5 are supplied to flow cell 61. Flow cell 61 forms a flow of the measurement specimen in a state of being enclosed in a sheath liquid that is the diluent.

Light source unit 62 is a semiconductor laser light source, which applies red laser light having a wavelength of 633 nm onto flow cell 61.

Light receivers 63 to 65 receive light emitted from the measurement specimen when the light is applied onto the flow of the measurement specimen in flow cell 61, and output electrical signals corresponding to the intensity of the received light. As light receivers 63 to 65, avalanche photodiodes, photodiodes or photomultiplier tubes can be adopted. In the following description, a direction connecting light source unit 62 to flow cell 61 is referred to as "X direction", and a direction perpendicular to the X direction is referred to as "Y direction". Dichroic mirror 66 is disposed on the Y-direction side of flow cell 61. Dichroic mirror 66 transmits fluorescence emitted from the measurement specimen, and reflects side scattered light emitted from the measurement specimen. Light receiver 63 is disposed on the Y-direction side of flow cell 61, and can receive the fluorescence transmitted through dichroic mirror 66. Light receiver 65 can receive the side scattered light reflected by dichroic mirror 66. Moreover, light receiver 64 is disposed on the X-direction side of flow cell 61. To be more specific, light receiver 64 is disposed on the opposite side of flow cell 61 from light source unit 62. Light receiver 64 can receive forward scattered light emitted from the measurement specimen.

Note that the side scattered light may not be light scattered in a 90° direction (Y direction) to the X direction that is the optical axis direction of light source unit 62. Light scattered in a direction of 80° to 100° to the X direction can be used as the side scattered light. Also, the forward scattered light may not be light scattered in the X direction that is the optical axis direction of light source unit 62. Light scattered in a direction of −10° to 10° to the X direction can be used as the forward scattered light.

Light receivers 63 to 65 each output an analog signal indicating received light intensity. Hereinafter, the analog signal outputted from light receiver 63 is referred to as "fluorescent signal", the analog signal outputted from light receiver 64 is referred to as "forward scattered light signal", and the analog signal outputted from light receiver 65 is referred to as "side scattered light signal".

Signal processing circuit 81 performs signal processing on the analog signals outputted by light receivers 63 to 65. Signal processing circuit 81 extracts peak values of pulses included in the fluorescent signal, forward scattered light signal, and side scattered light signal, as feature parameters. Hereinafter, the peak value of the fluorescent signal is referred to as "fluorescence intensity", the peak value of the forward scattered light signal is referred to as "forward scattered light intensity", and the peak value of the side scattered light signal is referred to as "side scattered light intensity".

Microcomputer 82 controls aspirator 4, specimen preparation unit 5, detector 6, signal processing circuit 81, and communication interface 83.

Communication interface 83 is connected to analysis unit 3 through a communication cable. Measurement unit 2 performs data communication with analysis unit 3 through communication interface 83. When measurement of the blood specimen is performed, communication interface 83 transmits measured data including feature parameters to analysis unit 3.

Figure 2:
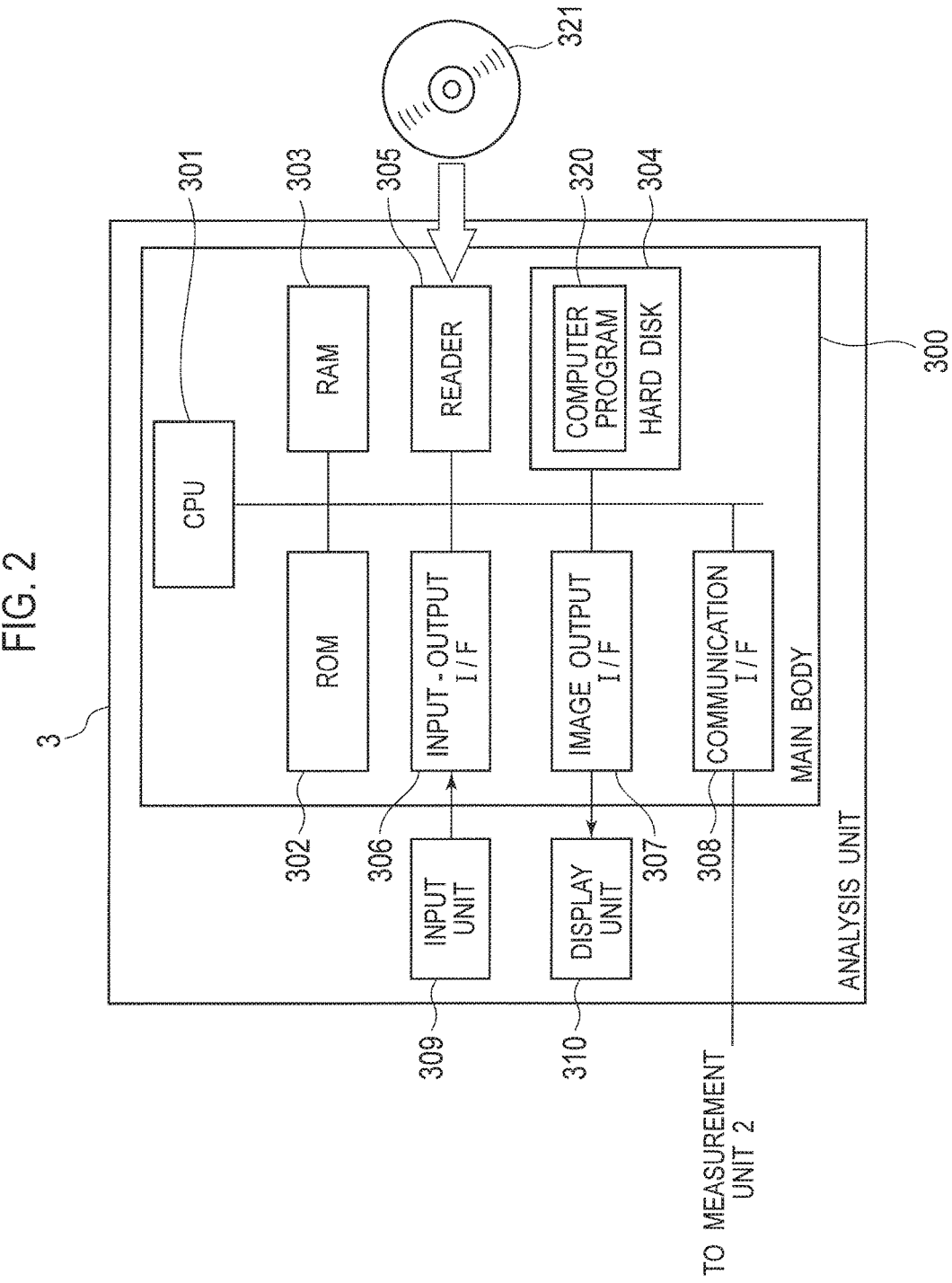
FIG. 2 is a block diagram illustrating a configuration of an analysis unit.

With reference to FIG. 2, a configuration of analysis unit 3 is described. Analysis unit 3 includes main body 300, input unit 309, and display unit 310. Main body 300 includes CPU (Central Processing Unit) 301, ROM (Read Only Memory) 302, RAM (Random Access Memory) 303, hard disk 304, reader 305, input-output interface 306, image output interface 307, and communication interface 308.

CPU 301 executes a computer program stored in ROM 302 and a computer program loaded onto RAM 303. RAM 303 is used to read the computer programs stored in ROM 302 and hard disk 304. RAM 303 is also used as a work area for CPU 301 during execution of the computer programs.

Computer program 320 to analyze the measured data from measurement unit 2 and to display the analysis result is installed into hard disk 304.

Reader 305 is a flexible disk drive, a CD-ROM drive, a DVD-ROM drive or the like, and can read computer programs or data stored in portable storage medium 321. Also, portable storage medium 321 stores computer program 320 to cause the computer to function as analysis unit 3. Computer program 320 read from portable storage medium 321 is installed into hard disk 304.

Input unit 309 is connected to input-output interface 306. Display unit 310 is connected to image output interface 307.

Communication interface 308 is connected to communication interface 83 in measurement unit 2.

Operations of Blood Analyzer

Figure 3:
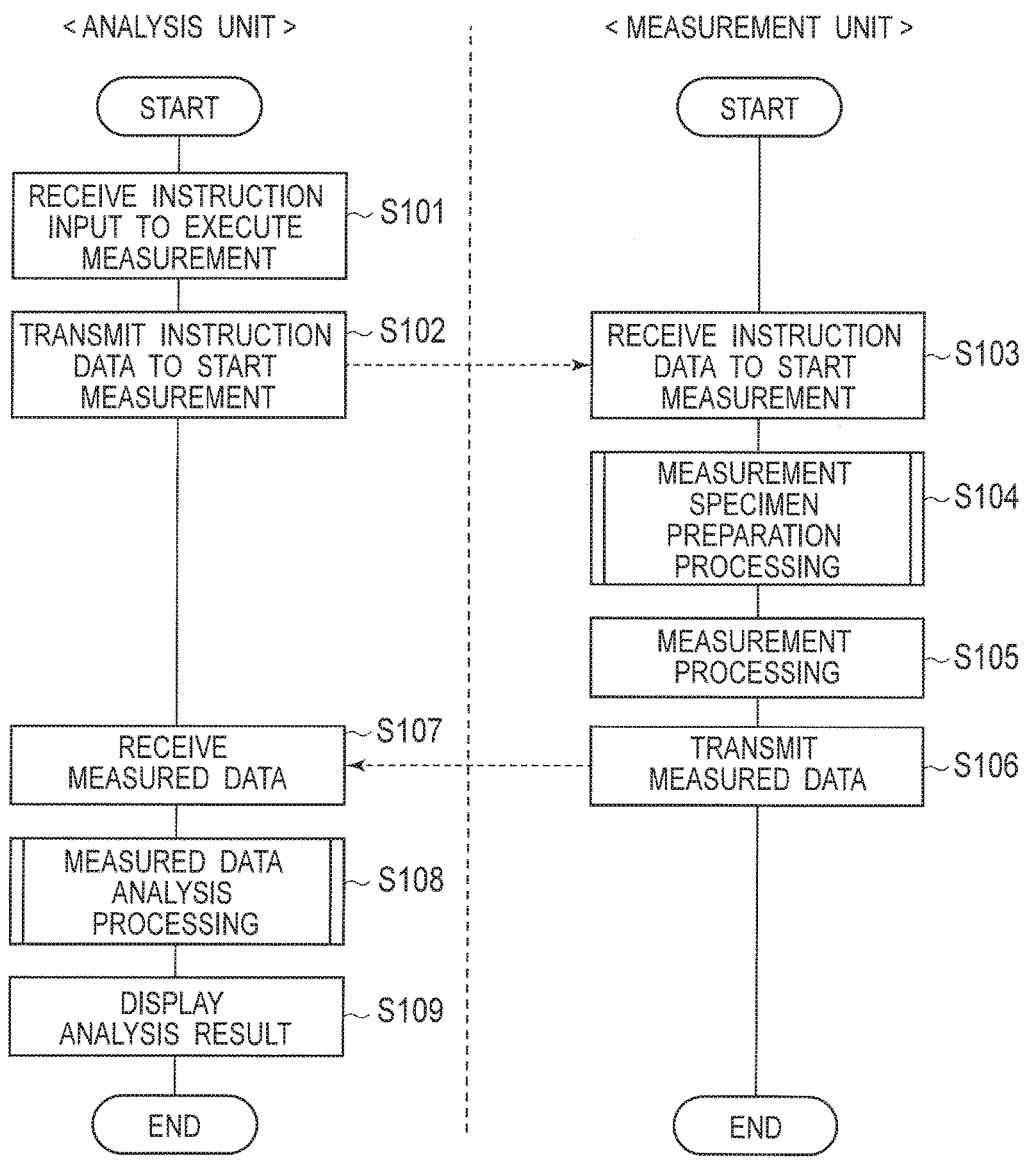
FIG. 3 is a flowchart illustrating a flow of operations by the blood analyzer according to the embodiment.

With reference to FIG. 3, operations of blood analyzer 1 are described.

First, CPU 301 in analysis unit 3 receives an instruction to execute measurement from a user through input unit 309 (Step S101). Upon receipt of the instruction to execute measurement, CPU 301 transmits instruction data to start measurement to measurement unit 2 (Step S102), and measurement unit 2 receives the instruction data (Step S103). Microcomputer 82 executes measurement specimen preparation processing (Step S104) and executes measurement processing (Step S105).

Figure 4:
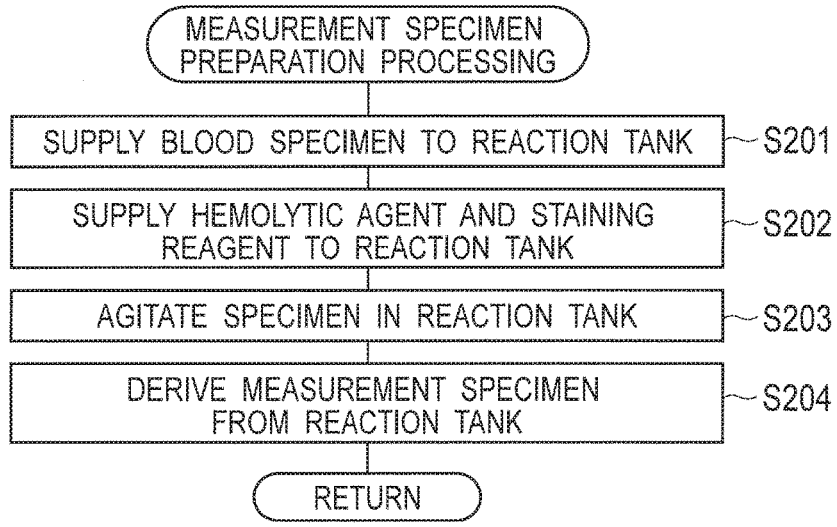
FIG. 4 is a flowchart illustrating a procedure of measurement specimen preparation processing.

With reference to FIG. 4, the measurement specimen preparation processing is described. Microcomputer 82 controls aspirator 4 to supply a predetermined amount of blood specimen to reaction tank 54 (Step S201). Next, microcomputer 82 controls specimen preparation unit 5 to supply a predetermined amount of hemolytic agent to reaction tank 54 from reagent container 52, and to supply a predetermined amount of staining reagent to reaction tank 54 from reagent container 53 (Step S202).

Reaction tank 54 is heated to a predetermined temperature by a heater. The mixture in reaction tank 54 is agitated in the heated state (Step S203). Through the operation of Steps S201 to S203, specimen preparation unit 5 prepares a measurement specimen in reaction tank 54. Microcomputer 82 controls specimen preparation unit 5 to derive the measurement specimen from reaction tank 54 to detector 6 (Step S204).

Upon completion of the processing of Step S204, microcomputer 82 returns the processing to the main routine.

Referring back to FIG. 3, detector 6 measures the measurement specimen in the measurement processing. In the measurement processing, specimen preparation unit 5 supplies the measurement specimen together with the sheath liquid to flow cell 61, and the measurement specimen flows through flow cell 61. Light source unit 62 applies light onto the flow of the measurement specimen in flow cell 61.

When the measurement specimen flows through flow cell 61, particles such as white blood cells, nucleated red blood cells, giant platelets, and red blood cell ghosts which are red blood cells hemolyzed by hemolyzation processing sequentially pass through flow cell 61. The white blood cells and the nucleated red blood cells each have a nucleus, and thus are stained by the staining reagent. The "pseudo-nucleated" giant platelets have granules therein stained by the staining reagent. The red blood cell ghosts each have no nucleus, and thus are hardly stained by the staining reagent.

Every time light is applied onto blood cells, the particles (white blood cells, nucleated red blood cells, giant platelets, and red blood cell ghosts) emit fluorescence, forward scattered light, and side scattered light. Light receiver 63 receives the fluorescence emitted from the particles. Light receiver 64 receives the forward scattered light emitted from the particles. Light receiver 65 receives the side scattered light emitted from the particles.

Light receivers 63, 64, and 65 output electrical signals corresponding to light reception levels as a fluorescent signal, a forward scattered light signal, and a side scattered light signal, respectively. Signal processing circuit 81 extracts fluorescence intensity from the fluorescent signal, forward scattered light intensity from the forward scattered light signal, and side scattered light intensity from the side scattered light signal.

After the measurement processing, microcomputer 82 transmits measured data including feature parameters to analysis unit 3 (Step S106), and then terminates the processing.

Analysis unit 3 receives the measured data (Step S107). Thereafter, CPU 301 executes measured data analysis processing to generate an analysis result of the blood specimen, and stores the analysis result in hard disk 304 (Step S108).

Figure 5:
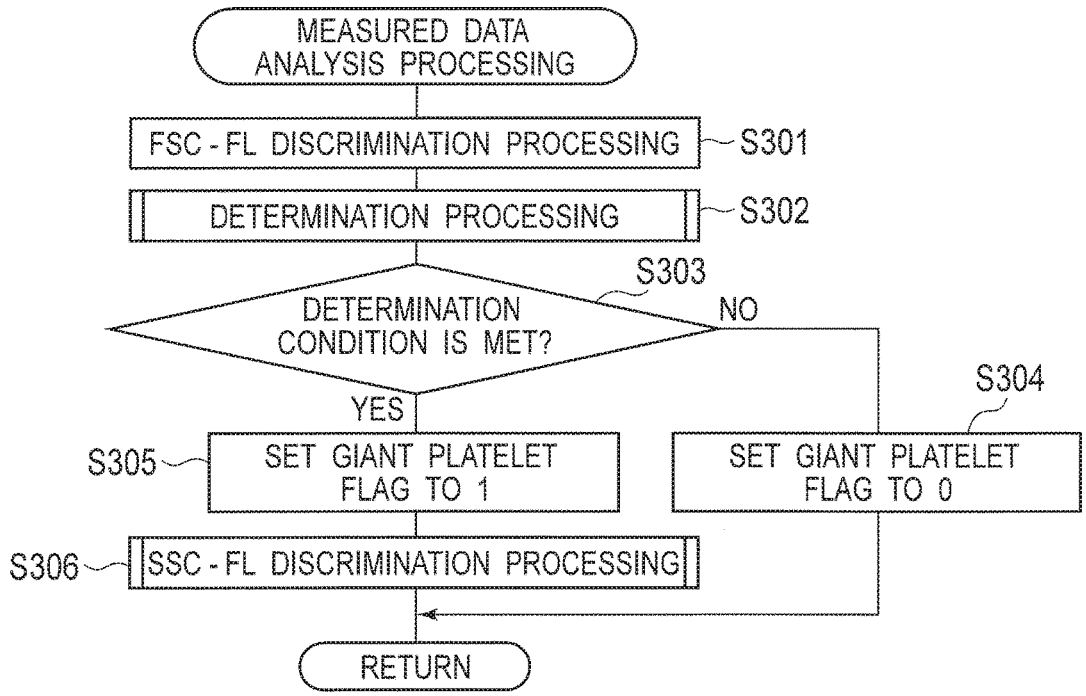
FIG. 5 is a flowchart illustrating a procedure of measured data analysis processing.

With reference to FIG. 5, the measured data analysis processing is described. As the measured data analysis processing is started, CPU 301 first executes FSC-FL discrimination processing using the forward scattered light intensity and fluorescence intensity included in the measured data (Step S301).

The FSC-FL discrimination processing discriminates a group of white blood cells from other groups of particles, based on the forward scattered light intensity and fluorescence intensity detected by detector 6. To be more specific, the FSC-FL discrimination processing discriminates among basophils, white blood cells other than the basophils, nucleated red blood cells, and red blood cell ghosts.

Figure 6:
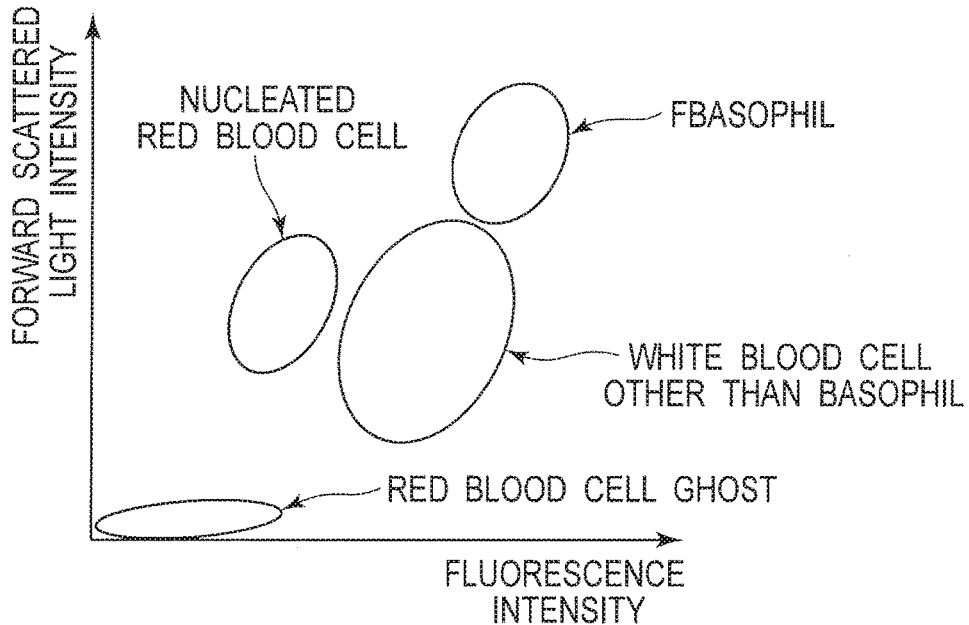
FIG. 6 is a diagram illustrating appearing regions of particle groups of basophils, white blood cells other than the basophils, nucleated red blood cells, and red blood cell ghosts in a scattergram with forward scattered light intensity as the vertical axis and fluorescence intensity as the horizontal axis.

Next, FIG. 6 is referred to. In a scattergram of FIG. 6, the vertical axis represents the forward scattered light intensity, while the horizontal axis represents the fluorescence intensity. The forward scattered light intensity is information reflecting the particle size. The white blood cells other than the basophils and the nucleated red blood cells substantially have the same size. Therefore, a group of the white blood cells other than the basophils substantially has the same forward scattered light intensity as a group of the nucleated red blood cells. Moreover, the white blood cells tend to have the stained portion retained, compared with the nucleated red blood cells, by the staining reagent described above, and thus have the fluorescence intensity higher than that of the nucleated red blood cells. Accordingly, the group of white blood cells other than the basophils has the fluorescence intensity higher than that of the group of nucleated red blood cells. Moreover, the external shape and the internal structure of each of the white blood cells change according to cell characteristics. Such a morphological difference appears as a difference in forward scattered light intensity. Therefore, a group of the basophils has higher forward scattered light intensity than the group of white blood cells other than the basophils. The red blood cell ghosts are smaller than the other particles, and are hardly stained by the staining reagent. Therefore, a group including the red blood cell ghosts has lower forward scattered light intensity and fluorescence intensity than the other particle groups.

In the FSC-FL discrimination processing, CPU 301 sets appearing regions for the basophils, the white blood cells other than the basophils, the nucleated red blood cells, and the red blood cell ghosts, for discrimination thereamong by regarding a particle group included in the appearing region of the basophils as the basophils, a particle group included in the appearing region of the white blood cells other than the basophils as the white blood cells other than the basophils, a particle group included in the appearing region of the nucleated red blood cells as the nucleated red blood cells, and a particle group included in the appearing region of the red blood cell ghosts as the red blood cells.

In discrimination between the white blood cells other than the basophils and the red blood cell ghosts, a particle number distribution in the forward scattered light intensity is used. CPU 301 detects a borderline between two groups in the particle number distribution, and sets a group appearing in a region where the forward scattered light intensity is above the borderline as a group of the white blood cells other than the basophils, and a group appearing in a region where the forward scattered light intensity is below the borderline as a group of the red blood cell ghosts.

Also, in the FSC-FL discrimination processing, CPU 301 counts the number of white blood cells and the number of nucleated red blood cells, and stores the count result in hard disk 304. To be more specific, CPU 301 separately counts the discriminated basophils and white blood cells other than the basophils, and sets the sum thereof as the number of white blood cells.

Figure 7:
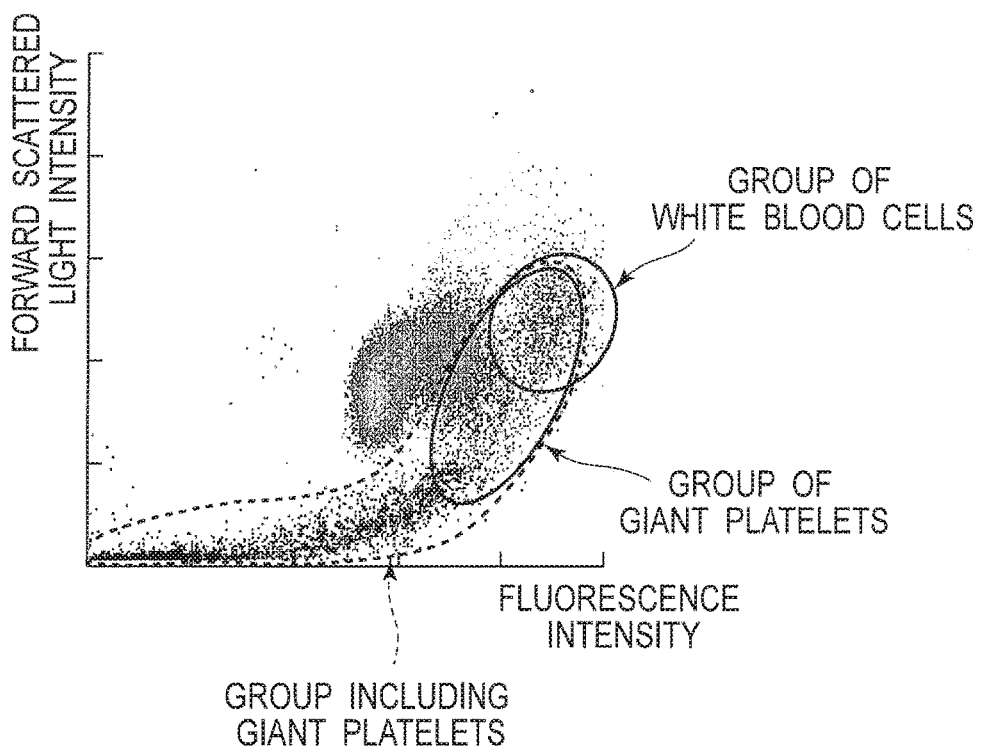
FIG. 7 is a diagram illustrating an example of a scattergram with forward scattered light intensity and fluorescence intensity as axes in a blood specimen in which giant platelets appear.

Referring back to FIG. 5, CPU 301 then executes determination processing (Step S302). In the result of the FSC-FL discrimination processing, giant platelets may appear in the appearing region of the white blood cells in the scattergram of the forward scattered light intensity and fluorescence intensity. In the case of a blood specimen containing giant platelets, a group of giant platelets appears to overlap with a group of white blood cells in the scattergram of the forward scattered light intensity and fluorescence intensity, as illustrated in FIG. 7. Moreover, the group of giant platelets and a group of red blood cell ghosts are combined and appear as one group. Hereinafter, a group obtained by the combination of the group of giant platelets and the group of red blood cell ghosts is referred to as the "group including giant platelets". In the determination processing, CPU 301 determines whether or not the group including giant platelets appears overlapping with the group of white blood cells.

Note that, as for information processing using a coordinate space in the following description, the information processing is performed in a virtual coordinate space, not in an actual coordinate space displayed by CPU 301.

Figure 8:
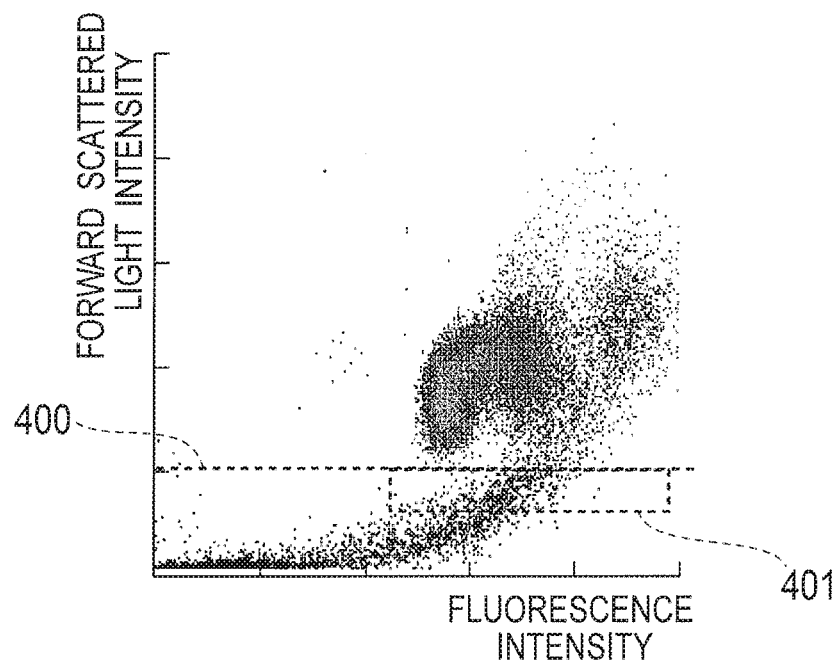
FIG. 8 is a diagram illustrating a scattergram with forward scattered light intensity and fluorescence intensity as axes for explaining determination processing.

The determination processing determines whether or not the result of the FSC-FL discrimination processing meets a predetermined condition (hereinafter referred to as the "determination condition"). The determination condition can be that the number of particles included in a predetermined region in the coordinate space with the forward scattered light intensity and the fluorescence intensity as axes exceeds a threshold. With reference to FIG. 8, the predetermined region is described. In the coordinate space of the forward scattered light intensity and fluorescence intensity illustrated in FIG. 8, predetermined region (hereinafter referred to as "determination region") 401 is provided on the side where the forward scattered light intensity is below borderline 400 used to discriminate the white blood cells other than the basophils from the red blood cell ghosts in the FSC-FL discrimination processing. Moreover, the range of the fluorescence intensity in determination region 401 is set as the range of fluorescence intensity in which white blood cells and giant platelets appear.

The determination condition may also include that the number of particles present on borderline 400 exceeds a predetermined threshold in the coordinate space of forward scattered light intensity and fluorescence intensity. In this embodiment, the determination condition includes a first condition that the number of particles present on borderline 400 exceeds a predetermined threshold (hereinafter referred to as the "first threshold") and a second condition that the number of particles included in determination region 401 exceeds a threshold (hereinafter referred to as the "second threshold") different from the first threshold.

Figure 9:
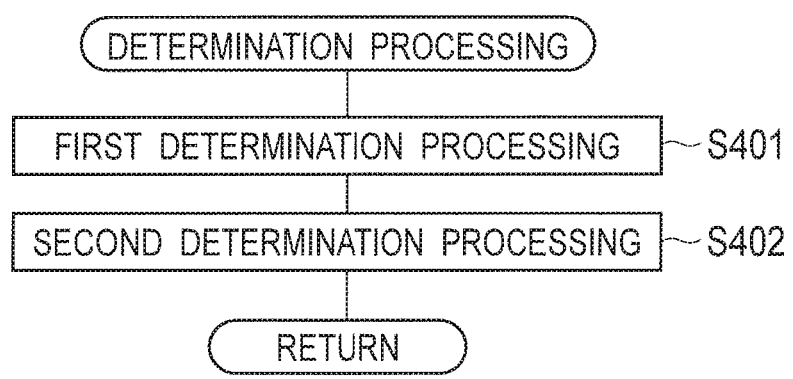
FIG. 9 is a flowchart illustrating a procedure of the determination processing.

With reference to FIG. 9, the determination processing is described in detail. In the determination processing, CPU 301 executes first determination processing (Step S401) and second determination processing (Step S402).

The first determination processing determines whether or not the result of the FSC-FL discrimination processing meets the first condition. In the first determination processing, CPU 301 counts the number of particles present on borderline 400, and determines whether or not the counted number of particles exceeds the first threshold. Borderline 400 is a borderline that divides a group of white blood cells other than basophils from a group of red blood cell ghosts. Therefore, when a group including giant platelets overlaps with the group of white blood cells other than the basophils, the group including giant platelets appears across borderline 400, and a given number or more of particles exist on borderline 400. On the other hand, when the group including giant platelets does not overlap with the group of white blood cells other than the basophils, the group of red blood cell ghosts appears away from the group of white blood cells other than the basophils. Therefore, almost no particle exists on borderline 400 between the group of white blood cells other than the basophils and the group of red blood cell ghosts. By determining whether or not the result of the FSC-FL discrimination processing meets the first condition as described above, it can be determined whether or not the group including giant platelets appears overlapping with the group of white blood cells.

The second determination processing is processing of determining whether or not the result of the FSC-FL discrimination processing meets the second condition. In the second determination processing, CPU 301 counts the number of particles included in determination region 401, and determines whether or not the counted number of particles exceeds the second threshold. When a blood specimen contains giant platelets, a group of giant platelets appears to extend to a group of white blood cells other than basophils from a group of red blood cell ghosts having forward scattered light intensity below borderline 400. Therefore, when a group including giant platelets overlaps with the group of white blood cells other than the basophils, the group including giant platelets appears to overlap with determination region 401, and a given number or more of particles exist indetermination region 401. On the other hand, when the group including giant platelets does not overlap with the group of white blood cells other than the basophils, almost no particle exists in determination region 401 between the group of white blood cells other than the basophils and the group of red blood cell ghosts. By determining whether or not the result of the FSC-FL discrimination processing meets the second condition as described above, it can be determined whether or not the group including giant platelets appears overlapping with the group of white blood cells.

After the second determination processing, CPU 301 terminates the determination processing.

Referring back to FIG. 5, when the determination result obtained by the determination processing does not meet at least one of the first and second determination conditions (NO in Step S303), CPU 301 sets a giant platelet flag about the appearance of giant platelets to 0 (Step S304).

On the other hand, when the determination result obtained by the determination processing meets both of the first and second determination conditions (YES in Step S303), CPU 301 sets the giant platelet flag to 1 (Step S305), and executes SSC-FL discrimination processing (Step S306).

Note that the CPU may be configured not to execute the SSC-FL discrimination processing when the determination result meets neither of the first and second conditions, and to execute the SSC-FL discrimination processing when the determination result meets any of the first and second conditions.

The giant platelet flag is provided in a specific region of RAM 303. When the giant platelet flag is 0, it indicates that the blood specimen is less likely to contain giant platelets. On the other hand, when the giant platelet flag is 1, it indicates that the blood specimen is suspected to contain giant platelets.

When the determination result does not meet the determination conditions, the blood specimen is considered to contain no giant platelets. Moreover, in this case, the group of giant platelets is considered not to appear overlapping with the group of white blood cells other than the basophils. Therefore, the number of white blood cells obtained by the FSC-FL discrimination processing is considered to be accurate, eliminating the need to execute the SSC-FL discrimination processing. Therefore, CPU 301 terminates the measured data analysis processing after setting the giant platelet flag to 0 in Step S304.

When the determination result meets the determination conditions, the blood specimen is considered to contain giant platelets. Moreover, in this case, the group of giant platelets is considered to appear overlapping with the group of white blood cells other than the basophils. Therefore, the number of white blood cells obtained by the FSC-FL discrimination processing is considered not to be accurate. In this case, the SSC-FL discrimination processing is executed to accurately discriminate between white blood cells and giant platelets, and the accurate number of white blood cells is obtained by recounting the white blood cells.

The SSC-FL discrimination processing is described. The SSC-FL discrimination processing discriminates white blood cells from giant platelets based on side scattered light intensity and fluorescence intensity. The side scattered light intensity is information reflecting the internal state of cells. The giant platelets substantially have the same size as the white blood cells, and thus cannot be accurately discriminated based on the forward scattered light intensity. In the SSC-FL discrimination processing, the side scattered light intensity and the fluorescence intensity are used to discriminate between the giant platelets and the white blood cells, which are different in internal structure.

To be more specific, in the SSC-FL discrimination processing, appearing regions are set for the white blood cells and the giant platelets, based on a distribution state of particles in a coordinate space with the side scattered light intensity and fluorescence intensity as axes, and discrimination between the white blood cells and the giant platelets is performed by regarding a particle group included in the appearing region of the white blood cells as the white blood cells and a particle group included in the appearing region of the giant platelets as the giant platelets. In the SSC-FL discrimination processing, the white blood cells and the giant platelets may be discriminated from each other based on the particle number distribution of particles in the coordinate space of the side scattered light intensity and fluorescence intensity. Alternatively, the white blood cells and the giant platelets may be discriminated from each other by clustering the particles based on the particle distribution state in the coordinate space of the side scattered light intensity and fluorescence intensity. In the discrimination by clustering, clustering of particles can be performed in a two-dimensional space with the side scattered light intensity and the fluorescence intensity as two orthogonal axes. Alternatively, clustering of particles can be performed in a three-dimensional space with the side scattered light intensity, the fluorescence intensity, and the forward scattered light intensity as three orthogonal axes.

In the SSC-FL discrimination processing, based on the particle distribution state in the coordinate space of the side scattered light intensity and the fluorescence intensity, a particle group in which the higher the side scattered light intensity, the higher the fluorescence intensity is discriminated as a group of white blood cells, while particles appearing in a region having lower side scattered light intensity than that of the group of white blood cells are discriminated as giant platelets.

Figure 10:
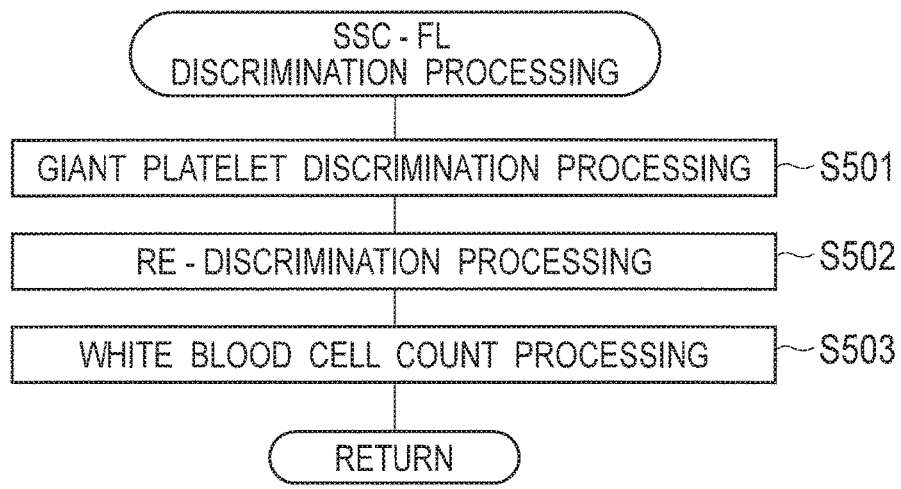
FIG. 10 is a flowchart illustrating a procedure of SSC-FL discrimination processing.

Next, FIG. 10 is referred to. As illustrated in FIG. 10, the SSC-FL discrimination processing includes giant platelet discrimination processing (Step S501), re-discrimination processing (Step S502), and white blood cell count processing (Step S503).

Figure 11:
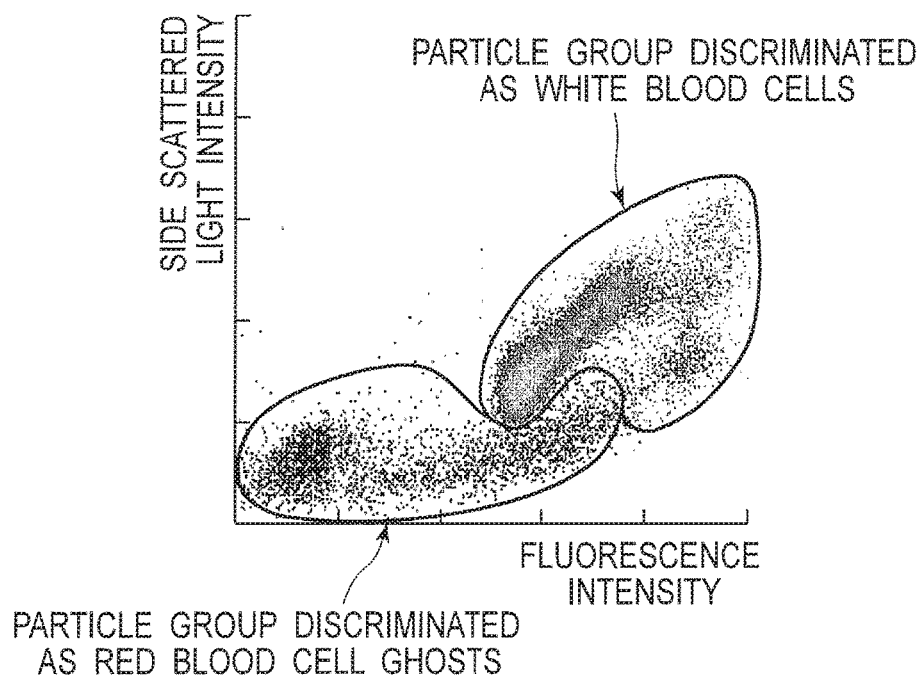
FIG. 11 is a diagram illustrating a scattergram with side scattered light intensity and fluorescence intensity as axes, which are obtained as a result of FSC-FL discrimination processing.

The giant platelet discrimination processing is described. When the result of the FSC-FL discrimination processing meets both of the first and second conditions, a particle group (hereinafter referred to as the "first target particle group") discriminated as the basophils and the white blood cells other than the basophils is considered to include the white blood cells and the giant platelets. The giant platelet discrimination processing is processing on the first target particle group to discriminate between a group of white blood cells and a group including giant platelets. To be more specific, the giant platelet discrimination processing discriminates between a group of white blood cells and a group including giant platelets in the first target particle group, based on the numbers of particles in the first target particle group at respective positions in a direction intersecting with a maximum dispersion direction of the first target particle group in a coordinate space with the side scattered light intensity and the fluorescence intensity as coordinate axes. The group (collection of the group of basophils and the group of white blood cells other than the basophils) discriminated as the white blood cells in FIG. 11 is the first target particle group.

Figure 12A:
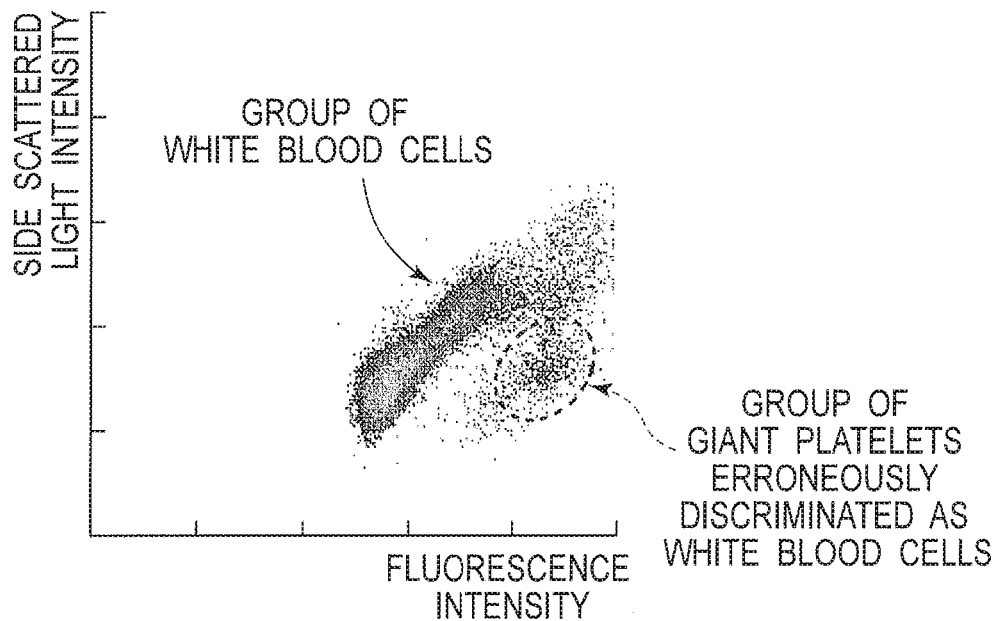
FIG. 12A is a diagram illustrating a scattergram with the side scattered light intensity and the fluorescence intensity as axes for explaining giant platelet discrimination processing.

Next, FIGS. 12A to 12E are referred to. A particle group illustrated in FIG. 12A is the first target particle group. The first target particle group includes a group of giant platelets in a region indicated by the broken line in FIG. 12A. As illustrated in FIG. 12A, a group of white blood cells tends to have side scattered light intensity proportional to fluorescence intensity. More specifically, in the coordinate space of the side scattered light intensity and the fluorescence intensity, the group of white blood cells appears as a particle group in which the higher the side scattered light intensity, the higher the fluorescence intensity. Moreover, in the coordinate space of the side scattered light intensity and the fluorescence intensity, a group of giant platelets erroneously discriminated as the white blood cells appears in a region next to the group of white blood cells.

Figure 12B:
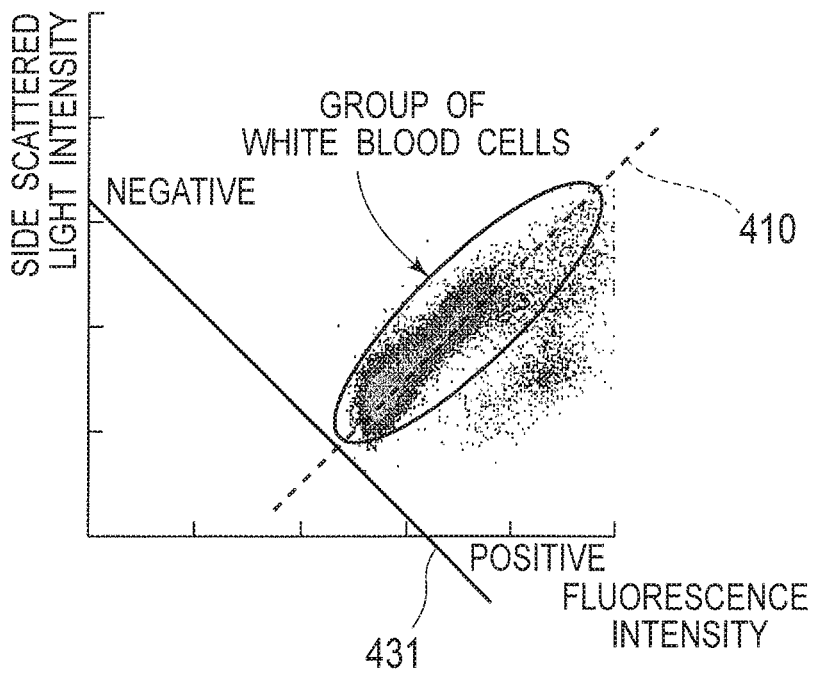
FIG. 12B is a diagram illustrating a scattergram with the side scattered light intensity and the fluorescence intensity as axes for explaining the giant platelet discrimination processing.

As illustrated in FIG. 12B, in the giant platelet discrimination processing, CPU 301 sets line 431 extending along the plane including the coordinate axis of the side scattered light intensity and the coordinate axis of the fluorescence intensity. To be more specific, CPU 301 rotates the coordinate space of the side scattered light intensity and the fluorescence intensity by a predetermined angle, and sets the horizontal axis in this event as line 431. Line 431 extends in a direction tilted to the coordinate axis of the side scattered light intensity and the coordinate axis of the fluorescence intensity, more specifically, line 431 extends in a direction tilted clockwise at 45° to the coordinate axis of the fluorescence intensity. In other words, line 431 extends in a direction intersecting with the maximum dispersion direction in the distribution of the first target particle group. Note that line 431 may be a straight line extending in a direction tilted clockwise at an angle other than 45° to the coordinate axis of the fluorescence intensity. For example, a straight line extending in a direction tilted clockwise at 30° to the coordinate axis of the fluorescence intensity can be set as line 431.

The coordinate axes of the side scattered light intensity and fluorescence intensity are logarithmic axes. The group of white blood cells tends to be proportional to the side scattered light intensity and the fluorescence intensity. Therefore, since both of the coordinate axes are the logarithmic axes, the group of white blood cells is distributed along straight line 410 extending obliquely to the coordinate axes of the side scattered light intensity and the fluorescence intensity. More specifically, the direction along straight line 410 is the maximum dispersion direction of the group of white blood cells. Line 431 can be set to intersect with straight line 410. To be more specific, line 431 can be set perpendicular to line 410. Alternatively, the coordinate axes of the side scattered light intensity and fluorescence intensity may be linear axes. In this case, again, the group of white blood cells is distributed along a straight line extending obliquely to the coordinate axes of the side scattered light intensity and the fluorescence intensity.

Figure 12C:
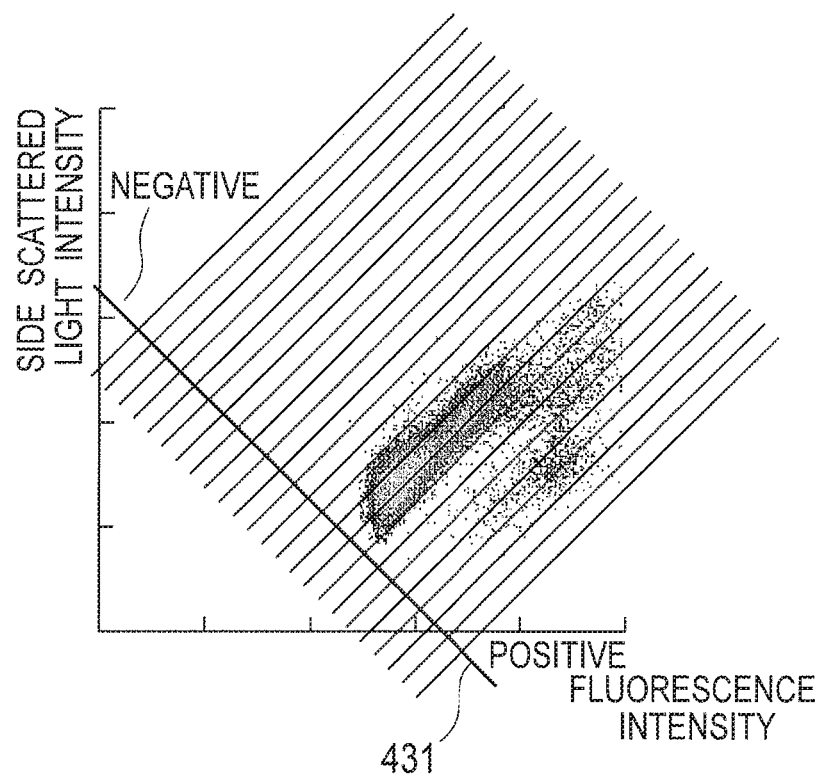
FIG. 12C is a diagram illustrating a scattergram with the side scattered light intensity and the fluorescence intensity as axes for explaining the giant platelet discrimination processing.

In the giant platelet discrimination processing, CPU 301 generates a particle number distribution of the first target particle group on line 431. To be more specific, as illustrated in FIG. 12C, CPU 301 counts particle groups included in divided regions in the extending direction of line 431, thereby obtaining a particle number distribution (histogram) on line 431.

Figure 12D:
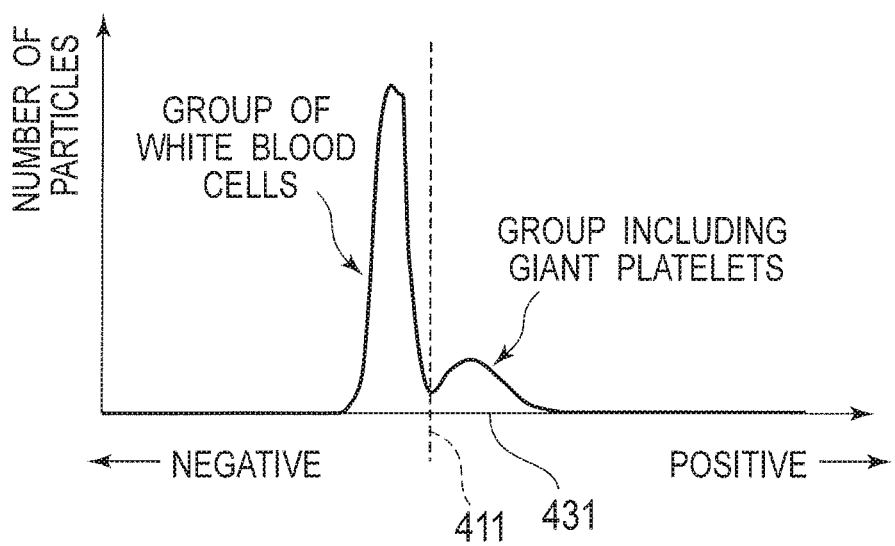
FIG. 12D is a diagram illustrating a particle number distribution for explaining the giant platelet discrimination processing.
Figure 12E:
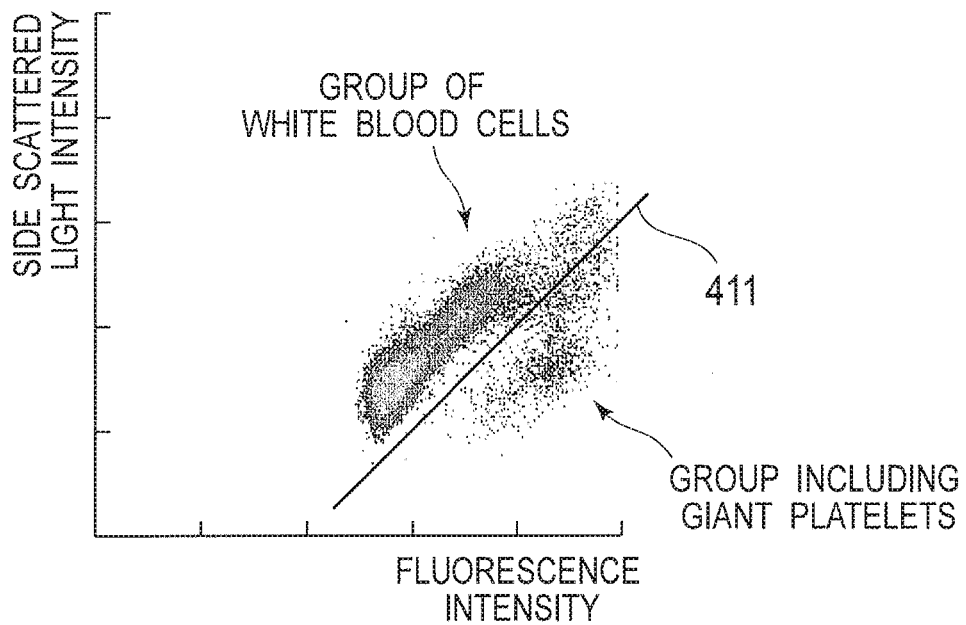
FIG. 12E is a diagram illustrating a scattergram with the side scattered light intensity and the fluorescence intensity as axes for explaining the giant platelet discrimination processing.

Here, it is assumed that, in the direction along line 431, a direction in which the fluorescence intensity increases, that is, a direction in which the side scattered light intensity decreases is a positive direction, and a direction in which the fluorescence intensity decreases, that is, a direction in which the side scattered light intensity increases is a negative direction. The group of giant platelets erroneously discriminated as the white blood cells appears along the group of white blood cells in a region closer to the positive side of line 431 than the group of white blood cells. CPU 301 sets borderline 411 by detecting the valley of the particle number distribution as illustrated in FIG. 12D, thereby discriminating a group of white blood cells appearing on the negative side of line 431 with respect to borderline 411 from a group including giant platelets appearing on the positive side of line 431 with respect to borderline 411. As illustrated in FIG. 12E, in the coordinate space of the side scattered light intensity and the fluorescence intensity, borderline 411 is a straight line extending in a direction perpendicular to line 431.

Figure 13:
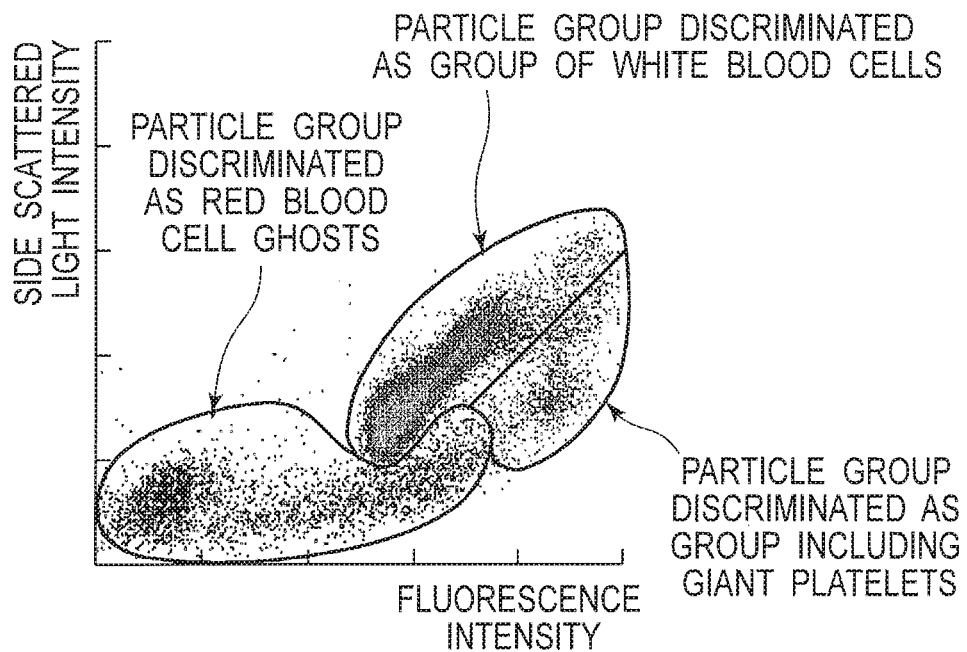
FIG. 13 is a diagram illustrating a scattergram with the side scattered light intensity and the fluorescence intensity as axes, which are obtained as a result of the giant platelet discrimination processing.

White blood cells are distributed on the negative side of line 431 with respect to borderline 411. Therefore, the white blood cells can be accurately discriminated by borderline 411. Moreover, as illustrated in FIG. 13, in the coordinate space of the side scattered light intensity and the fluorescence intensity, the particle group discriminated as the group including giant platelets in the giant platelet discrimination processing appears to be continuous with the particle group discriminated as red blood cell ghosts in the FSC-FL discrimination processing.

Next, the re-discrimination processing is described. The re-discrimination processing is processing on the group including giant platelets obtained by the giant platelet discrimination processing, to discriminate between a group of white blood cells and a group including giant platelets.

FIGS. 14A to 14E are referred to. In the re-discrimination processing, the particle group discriminated as the group including giant platelets in the giant platelet discrimination processing is set as a processing target. More specifically, in the re-discrimination processing, a particle group included in a region on the positive side of line 431 with respect to borderline 411 set in the giant platelet discrimination processing is set as the processing target (see FIG. 14A). Hereinafter, the particle group to be processed in the re-discrimination processing is referred to as the "second target particle group". The re-discrimination processing discriminates between a group of white blood cells and a group including giant platelets in the second target particle group, based on the numbers of particles in the second target particle group at respective positions in a direction different from the extending direction of line 431 in the coordinate space of the side scattered light intensity and the fluorescence intensity.

Figure 14A:
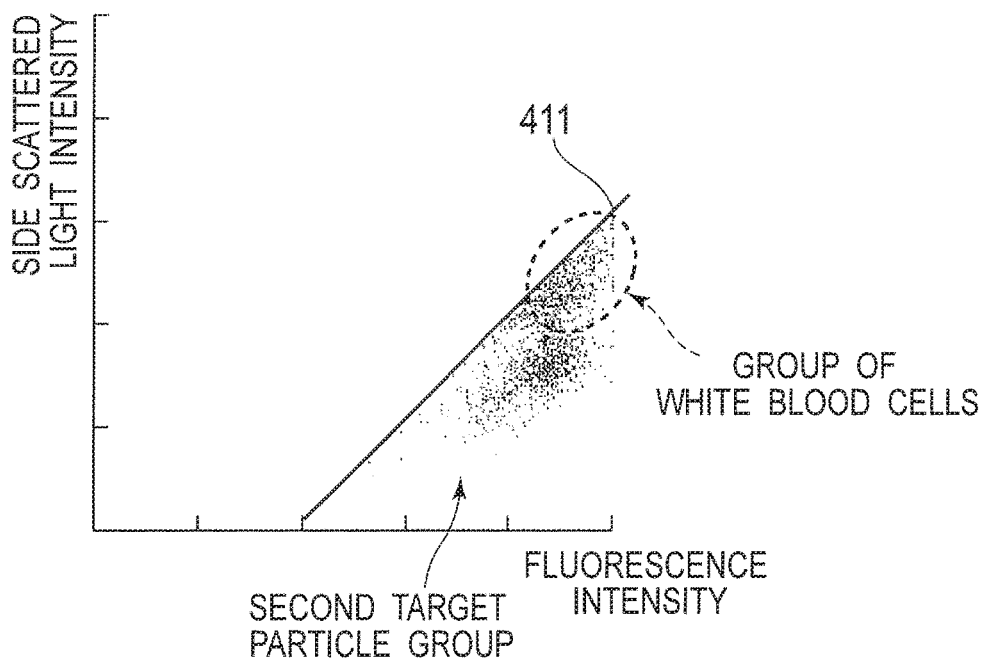
FIG. 14A is a diagram illustrating a scattergram with the side scattered light intensity and the fluorescence intensity as axes for explaining re-discrimination processing.

The second target particle group includes a group of white blood cells in a region indicated by the broken line in FIG. 14A. As illustrated in FIG. 14A, in the coordinate space of the side scattered light intensity and the fluorescence intensity, the group of white blood cells in the second target particle group appears in a region with higher side scattered light intensity than the group including giant platelets.

Figure 14B:
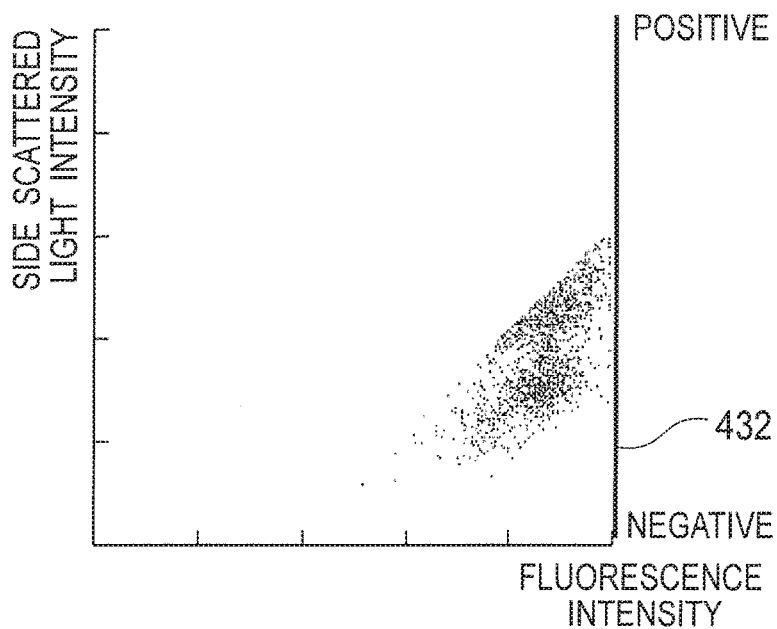
FIG. 14B is a diagram illustrating a scattergram with the side scattered light intensity and the fluorescence intensity as axes for explaining the re-discrimination processing.

As illustrated in FIG. 14B, in the re-discrimination processing, CPU 301 sets line 432, which is different from line 431 and extends along the plane including the coordinate axes of the side scattered light intensity and the fluorescence intensity. To be more specific, CPU 301 further rotates the coordinate space of the side scattered light intensity and the fluorescence intensity by a predetermined angle, and sets the horizontal axis in this event as line 432. Line 432 extends in a direction tilted to line 431, more specifically, extends in a direction tilted clockwise at 45° to line 431. Line 432 is a straight line parallel to the coordinate axis of the side scattered light intensity. In other words, line 432 extends in a direction intersecting with the second target particle group. Note that line 432 may be a straight line extending in a direction tilted clockwise at an angle other than 45° to line 431. For example, a straight line extending in a direction tilted clockwise at 30° to line 431 can be set as line 432.

Figure 14C:
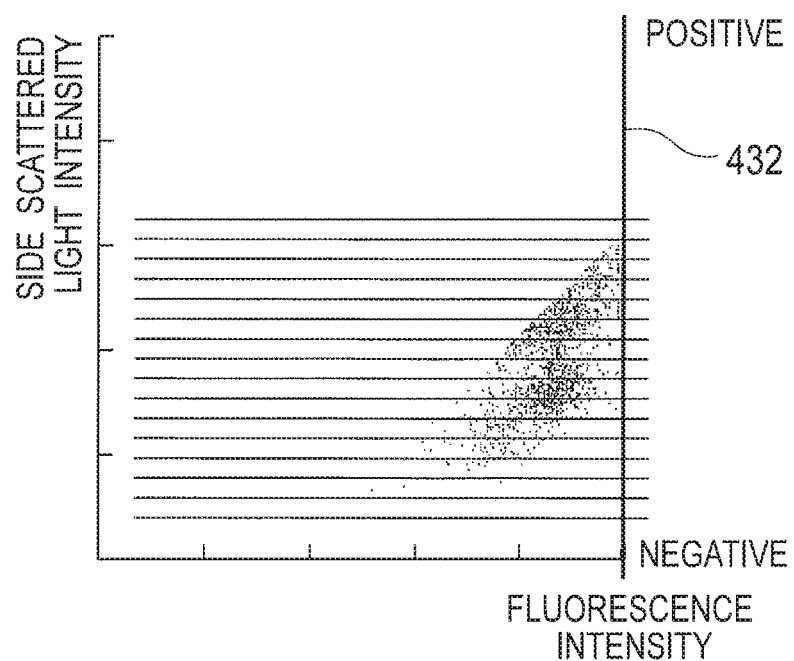
FIG. 14C is a diagram illustrating a scattergram with the side scattered light intensity and the fluorescence intensity as axes for explaining the re-discrimination processing.

In the re-discrimination processing, CPU 301 generates a particle number distribution of the second target particle group on line 432. To be more specific, as illustrated in FIG. 14C, CPU 301 counts particle groups included in divided regions in the extending direction of line 432, thereby obtaining a particle number distribution (histogram) on line 432.

Figure 14D:
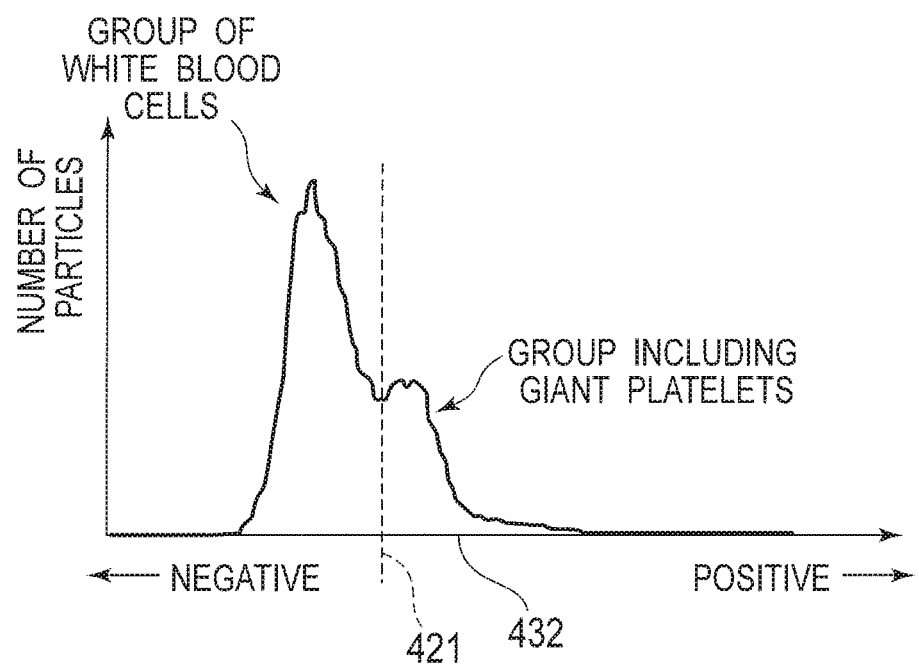
FIG. 14D is a diagram illustrating a particle number distribution for explaining the re-discrimination processing.
Figure 14E:
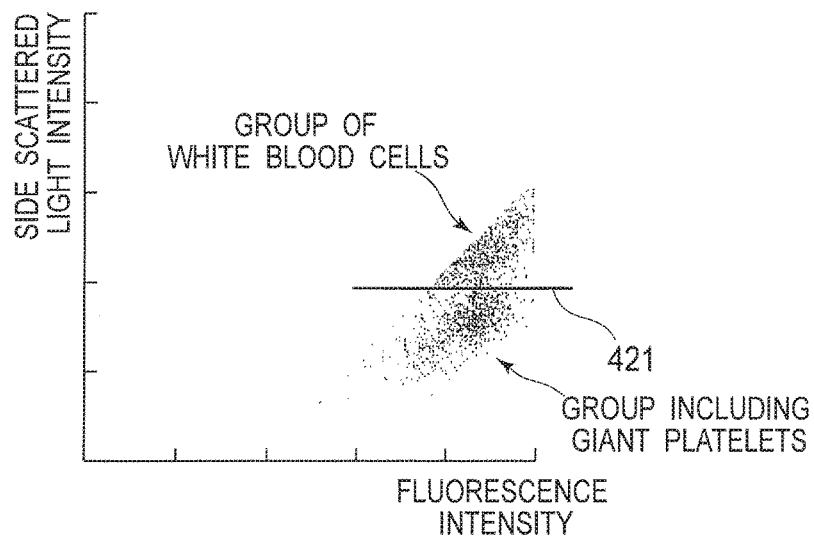
FIG. 14E is a diagram illustrating a scattergram with the side scattered light intensity and the fluorescence intensity as axes for explaining the re-discrimination processing.

Here, it is assumed that, in the direction along line 432, a direction in which the side scattered light intensity increases is a positive direction and a direction in which the side scattered light intensity decreases is a negative direction. The group of white blood cells in the second target particle group appears in a region closer to the positive side of line 432 than the group including giant platelets. CPU 301 sets borderline 421 by detecting the valley of the particle number distribution as illustrated in FIG. 14D, thereby discriminating a group of white blood cells appearing in a region on the positive side of line 432 with respect to borderline 421 from a group including giant platelets appearing in a region on the negative side of line 432 with respect to borderline 421. As illustrated in FIG. 14E, in the coordinate space of the side scattered light intensity and the fluorescence intensity, borderline 421 is a straight line extending in a direction perpendicular to line 432.

Figure 15:
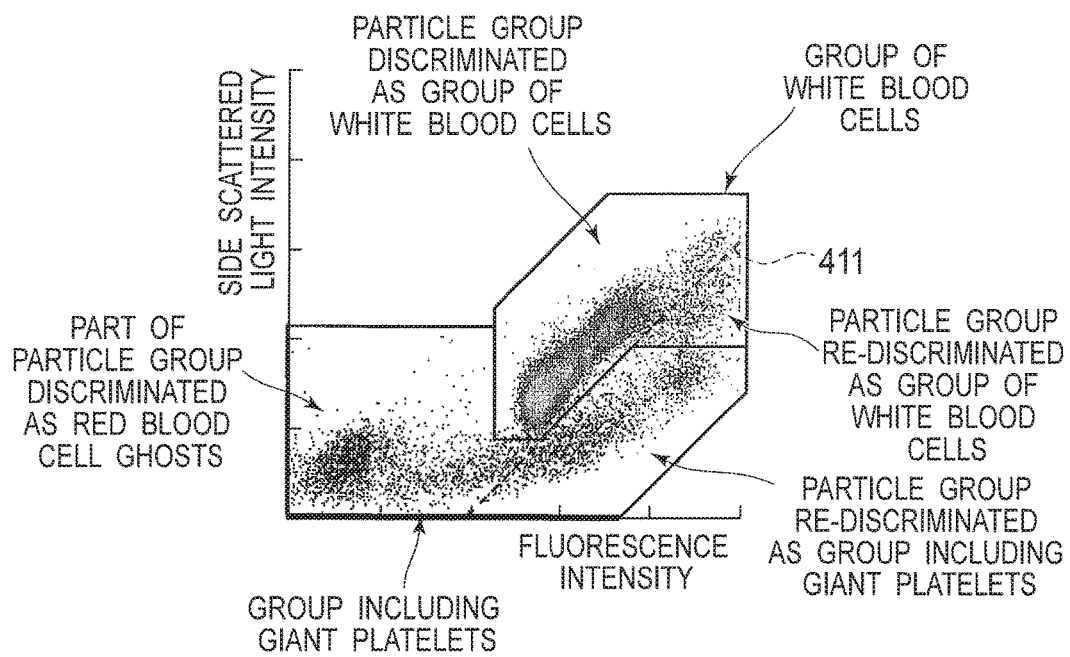
FIG. 15 is a diagram illustrating an example of a scattergram with forward scattered light intensity and fluorescence intensity as axes, which are obtained as a result of the SSC-FL discrimination processing.

In the white blood cell count processing, CPU 301 counts white blood cells assuming that a particle group obtained by combining the particle group discriminated as the group of white blood cells in the giant platelet discrimination processing with the particle group re-discriminated from the group of white blood cells in the re-discrimination processing is the group of white blood cells (see FIG. 15) and stores the count result in hard disk 304. In this event, CPU 301 replaces the count result of the white blood cells in the FSC-FL discrimination processing with the count result of the white blood cells in the SSC-FL discrimination processing. Moreover, CPU 301 sets a particle group obtained by combining the particle group re-discriminated as the group including giant platelets in the re-discrimination processing with the particle group on the positive side of line 431 with respect to borderline 411, among the particle groups discriminated as the red blood cell ghosts in the FSC-FL discrimination processing, as the group including the giant platelets. Thus, CPU 301 terminates the measured data analysis processing and returns the processing to the main routine.

Note that, in the SSC-FL discrimination processing, only the giant platelet discrimination processing may be performed without performing the re-discrimination processing. Moreover, rather than two separate processing steps of the giant platelet discrimination processing and the re-discrimination processing, processing of setting a line extending along the plane including coordinate axes of side scattered light intensity and fluorescence intensity and discriminating particle groups based on the number of particles at positions on the set line may be executed three times or more. In this case, a different line can be set in each execution of the processing.

Furthermore, rather than just discriminating basophils, white blood cells other than the basophils, nucleated red blood cells, and giant platelets, red blood cells and platelets may be measured and counted. In this case, a reagent different from the hemolytic agent and staining reagent described above may be mixed with the blood specimen to prepare a measurement specimen for measuring red blood cells and platelets, which is different from the measurement specimen described above, and the prepared measurement specimen may be measured using a sheath flow DC detection method or the like. Moreover, the white blood cells may be classified into different types such as monocytes, lymphocytes, eosinophils, neutrophils, and basophils, and blood cells may be counted by type. In this case, a measurement specimen for classifying the white blood cells, which is different from the measurement specimen described above, may be prepared, and the prepared measurement specimen may be measured by flow cytometry or the like.

Referring back to FIG. 3, upon completion of the measured data analysis processing as described above, CPU 301 displays the analysis result on display unit 310 (Step S109) and then terminates the processing. The analysis result includes the measurement results, such as the number of white blood cells, the number of nucleated red blood cells, and the number of basophils, and reference information for diagnosis. When the result of the FSC-FL discrimination processing meets the determination condition in the determination processing, information suggesting the presence of giant platelets is displayed as the reference information.

On the other hand, when the result of the FSC-FL discrimination processing does not meet the determination condition in the determination processing, the number of white blood cells to be displayed is the number of particles discriminated as the white blood cells in the FSC-FL discrimination processing. In the FSC-FL discrimination processing, the white blood cells are discriminated based on the forward scattered light intensity and the fluorescence intensity. The white blood cells and the nucleated red blood cells are different in fluorescence intensity. Thus, the use of the fluorescence intensity enables accurate discrimination between the white blood cells and the nucleated red blood cells. Moreover, since the forward scattered light intensity is information reflecting the size of cells, the white blood cells different in size from the red blood cell ghosts can be accurately discriminated. Therefore, when the blood specimen is considered to contain no giant platelets, the accurate number of white blood cells can be presented by displaying the number of white blood cells discriminated in the FSC-FL discrimination processing.

In the case where the result of the FSC-FL discrimination processing meets the determination condition in the determination processing, the number of white blood cells displayed is the number of particles discriminated as the white blood cells in the SSC-FL discrimination processing. When the blood specimen is considered to contain giant platelets, there might be a case where the white blood cells could not be discriminated accurately in the FSC-FL discrimination processing. Therefore, in this case, the accurate number of white blood cells can be presented by displaying the number of the white blood cells accurately discriminated from the giant platelets in the SSC-FL discrimination processing.

Figure 16:
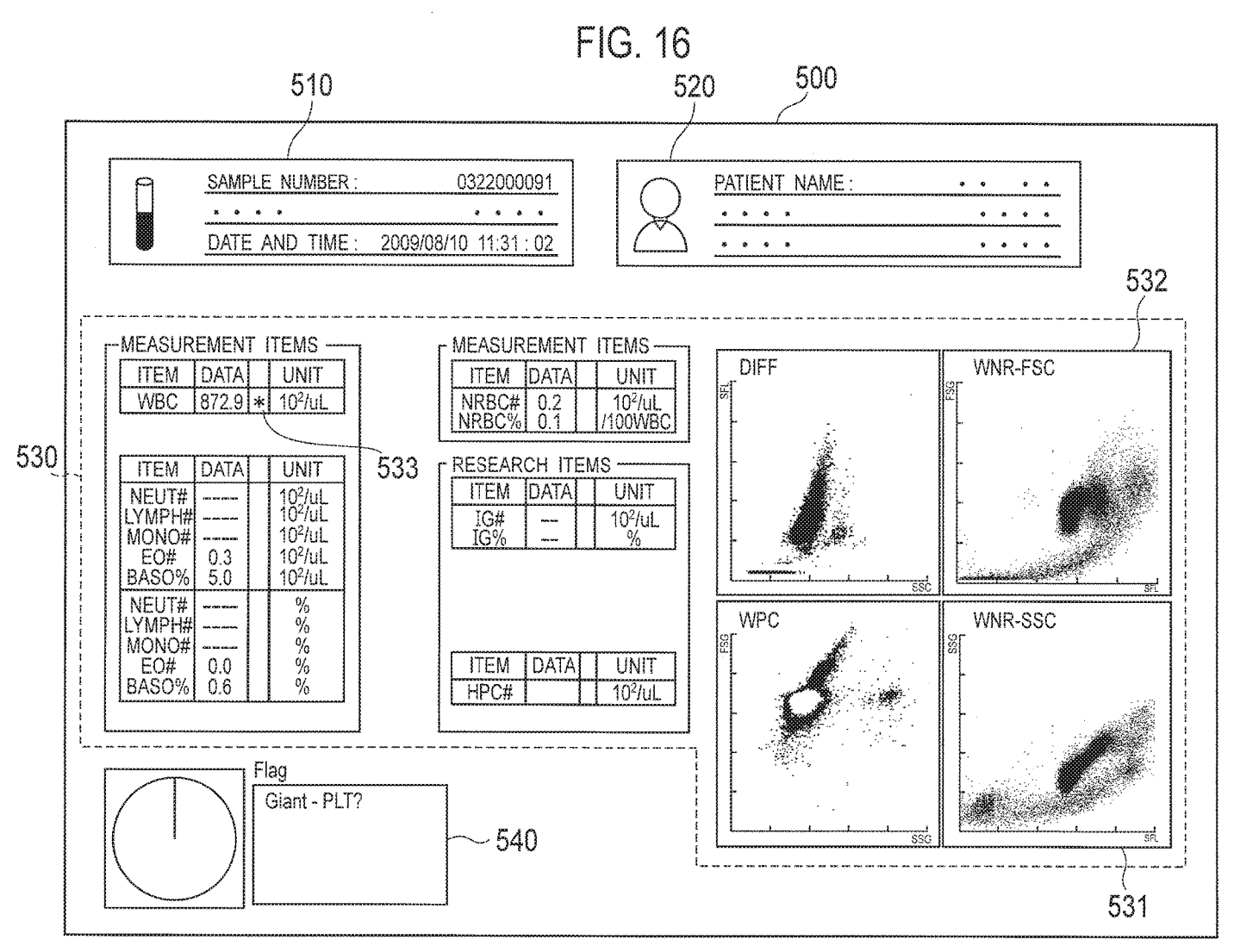

With reference to FIG. 16, the analysis result to be displayed is further described. Display unit 310 displays analysis result screen 500. Analysis result screen 500 includes specimen information display region 510, patient information display region 520, measurement result display region 530, and reference information display region 540.

Specimen information display region 510 displays information on a blood specimen used to obtain the analysis result displayed on analysis result screen 500. Patient information display region 520 displays information on a subject from whom the blood specimen is collected.

Measurement result display region 530 displays measured values of respective items obtained by the measured data analysis processing. The measured values displayed in measurement result display region 530 include measured values of the white blood cell count (WBC), nucleated red blood cell count (NRBC), and basophil count (BASO). Also, measurement result display region 530 includes: scattergram 531 that is a distribution map indicating a distribution state of particles in a coordinate space with side scattered light intensity and fluorescence intensity as coordinate axes; and scattergram 532 that is a distribution map indicating a distribution state of particles in a coordinate space with forward scattered light intensity and fluorescence intensity as coordinate axes.

Reference information display region 540 displays reference information to the user when a result that should be reported to the user is obtained, such as the suspicion that the blood specimen contains giant platelets, by the measured data analysis processing. When the giant platelet flag is set to 1 in the measured data analysis processing, reference information display region 540 displays "Giant-PLT?" that is information suggesting the presence of giant platelets. Note that the information suggesting the presence of the giant platelets is not limited to the above, but may be information indicating that the blood specimen is suspected to contain giant platelets. When the giant platelets are contained in the blood specimen, there is a possibility of diseases such as Bernard-Soulier syndrome, May-Hegglin anomaly, and idiopathic thrombocytopenic purpura. Therefore, diagnosis of such diseases can be supported by presenting the information indicating that the blood specimen is suspected to contain giant platelets.

Moreover, when the giant platelet flag is set to 1, the result of counting white blood cells obtained by the SSC-FL discrimination processing is displayed. In this case, the result of counting white blood cells obtained by the FSC-FL discrimination processing is considered not to be accurate, and the count result cannot be displayed. Therefore, in measurement result display region 530, "*" that is low reliability information 533 is displayed together with the measured value of the number of white blood cells. Thus, the user can be notified of the fact that the number of white blood cells displayed has low reliability.

The embodiments described above accurately discriminate white blood cells from giant platelets.

A program that realizes a blood analyze as described above may be stored on a non-transitory computer readable medium. The program stored in the recording medium is read into a system, such as a computer, so that the above-described blood analyze can be realized by executing the program while controlling the system. The medium includes such devices as a memory device, magnetic disk device, and an optical disk device, that are able to record the program. For example, the recording medium could be a memory card, a Blu-Ray disk, a CD-ROM (Compact Disc, read only memory), a DVD (Digital Versatile Disc), a ZIP disc, a JAZ disc, a MO (Magneto-optical) disc, DAT (Digital Audio Tape), or the like.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A blood analyzer comprising:
a specimen preparation unit comprising a reaction tank, the specimen preparation unit configured to prepare a measurement specimen by mixing in the reaction tank, a hemolytic agent that hemolyzes red blood cells, a staining dye that dyes nucleic acids, and a blood specimen;
a detector that detects intensity of side scattered light and intensity of fluorescence generated with application of light from the measurement specimen prepared by the specimen preparation unit; and
an analysis unit comprising:
a processor; and
a memory storing a program, wherein the processor is configured with the program to perform operations comprising:
receiving the intensity of side scattered light and the intensity of fluorescence detected by the detector;
discriminating white blood cells from giant platelets based on the intensity of side scattered light and the intensity of fluorescence detected by the detector; and
counting the white blood cells, wherein
the processor of the analysis unit is configured with the program to perform operations further comprising
executing giant platelet discrimination processing on a particle group including white blood cells to discriminate between a group of white blood cells and a group including giant platelets, based on the intensity of side scattered light and the intensity of fluorescence, and
executing re-discrimination processing on the group including the giant platelets obtained by the giant platelet discrimination processing to discriminate between a group of white blood cells and a group including giant platelets.

2. The blood analyzer according to claim 1, wherein
the processor of the analysis unit is configured with the program to perform operations further comprising
discriminating between the group of white blood cells and the group including giant platelets in the particle group, based on the numbers of particles in the particle group at respective positions in a direction intersecting with a maximum dispersion direction of the particle group including white blood cells in a coordinate space with the intensity of side scattered light and the intensity of fluorescence as coordinate axes.

3. The blood analyzer according to claim 2, wherein
the processor of the analysis unit is configured with the program to perform operations such that executing the re-discrimination processing comprises executing the re-discrimination processing on the particle group including giant platelets obtained by the giant platelet discrimination processing to discriminate between a group of white blood cells and a group including giant platelets, based on the numbers of particles in the particle group at respective positions in a direction different from the intersecting direction in the coordinate space.

4. A blood analyzer comprising:
a specimen preparation unit comprising a reaction tank, the specimen preparation unit configured to prepare a measurement specimen by mixing in the reaction tank, a hemolytic agent that hemolyzes red blood cells, a staining dye that dyes nucleic acids, and a blood specimen;
a detector that detects intensity of side scattered light and intensity of fluorescence generated with application of light from the measurement specimen prepared by the specimen preparation unit; and
an analysis unit comprising:
a processor; and
a memory storing a program, wherein the processor is configured with the program to perform operations comprising:
receiving the intensity of side scattered light and the intensity of fluorescence detected by the detector;
discriminating white blood cells from giant platelets based on the intensity of side scattered light and the intensity of fluorescence detected by the detector; and
counting the white blood cells, wherein
the detector further detects an intensity of forward scattered light generated with application of light from the measurement specimen prepared by the specimen preparation unit, and
the processor of the analysis unit is configured with the program to perform operations further comprising
executing first discrimination processing of discriminating a group of white blood cells from another particle group based on the intensity of forward scattered light and the intensity of fluorescence detected by the detector, and
executing second discrimination processing on the group of white blood cells obtained by the first discrimination processing, the second discrimination processing comprising discriminating white blood cells from giant platelets based on the intensity of side scattered light and the intensity of fluorescence when a result of the first discrimination processing meets a predetermined condition.

5. The blood analyzer according to claim 4, wherein the processor of the analysis unit is configured with the program to perform operations further comprising
executing the second discrimination processing on the group of white blood cells obtained by the first discrimination processing to discriminate between the group of white blood cells and a group including giant platelets based on the intensity of side scattered light and the intensity of fluorescence.

6. The blood analyzer according to claim 4, further comprising a display unit, wherein the processor of the analysis unit is configured with the program to perform operations further comprising
when the result of the first discrimination processing does not meet the predetermined condition, causing the display unit to display the number of particles, included in the group of white blood cells discriminated in the first discrimination processing, as the number of white blood cells, and
when the result of the first discrimination processing meets the predetermined condition, causing the display unit to display the number of particles, included in a group of white blood cells discriminated in the second discrimination processing, as the number of white blood cells.

7. The blood analyzer according to claim 4, further comprising a display unit, wherein the processor of the analysis unit is configured with the program to perform operations further comprising causing the display unit to display a particle distribution diagram with the intensity of side scattered light and the intensity of fluorescence as axes.

8. The blood analyzer according to claim 4, wherein the detector comprises
a flow cell through which the measurement specimen prepared by the specimen preparation unit flows,
a light source unit that applies laser light onto the measurement specimen flowing through the flow cell, and
a light receiver that receives side scattered light and fluorescence that the measurement specimen flowing through the flow cell generates with application of the laser light from the light source unit, and outputs a signal corresponding to the intensity of the received side scattered light and a signal corresponding to the intensity of the received fluorescence.

9. The blood analyzer according to claim 4, wherein the processor of the analysis unit is configured with the program to perform operations further comprising
setting an appearing region of the giant platelets based on the intensity of side scattered light and the intensity of fluorescence, and
discriminating a particle group included in the region as the giant platelets.

10. The blood analyzer according to claim 9, wherein the processor of the analysis unit is configured with the program to perform operations further comprising
discriminating a particle group in which the higher the intensity of side scattered light, the higher the intensity of fluorescence as a group of white blood cells, and setting a region where the intensity of side scattered light is lower than that in an appearing region of the group of white blood cells as the appearing region of the giant platelets.

11. The blood analyzer according to claim 4, wherein the predetermined condition comprises a condition in which the number of particles with both the intensity of forward scattered light and the intensity of fluorescence falling within a predetermined range, exceeds a threshold.

12. The blood analyzer according to claim 11, further comprising a display unit, wherein
the processor of the analysis unit is configured with the program to perform operations further comprising causing the display unit to display information indicating a possible presence of giant platelets when the result of the first discrimination processing meets the predetermined condition.

13. A blood analyzer comprising:
a specimen preparation unit comprising a reaction tank, the specimen preparation unit configured to prepare a measurement specimen by mixing in the reaction tank, a hemolytic agent that hemolyzes red blood cells, a staining dye that dyes nucleic acids, and a blood specimen;
a detector that detects intensity of side scattered light and intensity of fluorescence generated when light is applied onto the measurement specimen prepared by the specimen preparation unit;
a display unit; and
an analysis unit comprising:
a processor; and
a memory storing a program, wherein the processor is configured with the program to perform operations comprising:
receiving the intensity of side scattered light and the intensity of fluorescence detected by the detector;
detecting giant platelets in the measurement specimen based on the intensity of side scattered light and the intensity of fluorescence detected by the detector; and
causing information suggesting presence of the giant platelets to be displayed on the display unit, wherein
the detector further detects an intensity of forward scattered light generated with application of light from the measurement specimen prepared by the specimen preparation unit, and
the processor of the analysis unit is configured with the program to perform operations further comprising:
executing first discrimination processing of discriminating a group of white blood cells from another particle group based on the intensity of forward scattered light and the intensity of fluorescence detected by the detector; and
executing second discrimination processing on the group of white blood cells obtained by the first discrimination processing, the second discrimination processing comprising discriminating white blood cells from giant platelets based on the intensity of side scattered light and the intensity of fluorescence when a result of the first discrimination processing meets a predetermined condition.

14. A blood analyzer comprising:
a specimen preparation unit comprising a reaction tank, the specimen preparation unit configured to prepare a measurement specimen by mixing in the reaction tank, a hemolytic agent that hemolyzes red blood cells, a staining dye that dyes nucleic acids, and a blood specimen;
a detector that detects intensity of forward scattered light, intensity of side scattered light, and intensity of fluorescence generated with application of light from the measurement specimen prepared by the specimen preparation unit;
an analysis unit comprising:
  a processor; and
  a memory storing a program, wherein the processor is configured with the program to perform operations comprising:
    based on receiving the intensity of forward scattered light and the intensity of fluorescence detected by the detector, executing a first discrimination processing of discriminating white blood cells from other particles in the measurement specimen, based on the intensity of forward scattered light and the intensity of fluorescence detected by the detector, and counting the white blood cells; and
    based on receiving the intensity of side scattered light and the intensity of fluorescence detected by the detector, executing a second discrimination processing of discriminating white blood cells from other particles in the measurement specimen, based on the intensity of side scattered light and the intensity of fluorescence detected by the detector, and counting the white blood cells; and
a display unit,
wherein processor of the analysis unit is configured with the program to perform operations comprising
  causing the display unit to display the number of white blood cells obtained by the first discrimination processing when a result of the first discrimination processing does not meet a predetermined condition, and
  causing the display unit to display the number of white blood cells obtained by the second discrimination processing when the result of the first discrimination processing meets the predetermined condition.

15. A blood analyzer comprising:
a specimen preparation unit comprising a reaction tank, the specimen preparation unit configured to prepare a measurement specimen by mixing in the reaction tank, a hemolytic agent that hemolyzes red blood cells, a staining dye that dyes nucleic acids, and a blood specimen;
a detector that detects intensity of side scattered light and intensity of fluorescence generated when light is applied onto the measurement specimen prepared by the specimen preparation unit;
a display unit; and
an analysis unit comprising:
a processor; and
a memory storing a program, wherein the processor is configured with the program to perform operations comprising:
  receiving the intensity of side scattered light and the intensity of fluorescence detected by the detector;
  detecting giant platelets in the measurement specimen based on the intensity of side scattered light and the intensity of fluorescence detected by the detector; and
  causing information suggesting presence of the giant platelets to be displayed on the display unit, wherein
the processor of the analysis unit is configured with the program to perform operations further comprising
executing giant platelet discrimination processing on a particle group including white blood cells to discriminate between a group of white blood cells and a group including giant platelets, based on the intensity of side scattered light and the intensity of fluorescence, and
executing re-discrimination processing on the group including the giant platelets obtained by the giant platelet discrimination processing to discriminate between a group of white blood cells and a group including giant platelets.

* * * * *